United States Patent
Miyake et al.

(10) Patent No.: US 6,828,128 B2
(45) Date of Patent: Dec. 7, 2004

(54) β1,3-GALACTOSYLTRANSFERASE AND DNA ENCODING THE SAME

(75) Inventors: Katsuhide Miyake, Nagoya (JP); Masaki Watanabe, Nagoya (JP); Shinji Iijima, Nagoya (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/900,038

(22) Filed: Jul. 9, 2001

(65) Prior Publication Data

US 2002/0142425 A1 Oct. 3, 2002

(30) Foreign Application Priority Data

Jan. 5, 2001 (JP) ........................................ 2001-000392

(51) Int. Cl.⁷ ........................... C12P 19/18; C12N 9/10; C12N 1/21; C12N 15/52; C07H 21/04
(52) U.S. Cl. ...................... 435/97; 435/193; 435/252.3; 435/252.33; 435/320.1; 536/23.2
(58) Field of Search ........................ 435/97, 193, 252.3, 435/252.33, 320.1; 536/23.2

(56) References Cited

PUBLICATIONS

Isshiki, et al., "Cloning, Expression, and Characterization of a Novel . . . ", J. Biol. Chem., vol. 274, No. 18 (1999), pp. 12499–12507.

Amado, et al., "A Family of Human β3–Galactosyltransferases", J. Biol. Chem., vol. 273, No. 21 (1998), pp. 12770–12778.

Hennet, et al., "Genomic Cloning and Expression of Three Murine UDP–galactose: . . . ", J. Biol. Chem., vol. 273, No. 1 (1998), pp. 58–65.

Gilbert, et al., "Biosynthesis of Ganglioside Mimics . . . ", J. Biol. Chem., vol. 275, No. 6 (2000), pp. 3896–3906.

*Primary Examiner*—Elizabeth Slobodyansky
(74) *Attorney, Agent, or Firm*—Fitzpatrick, Cella, Harper & Scinto

(57) ABSTRACT

The present invention provides a protein having a β1,3-galactosyltransferase activity derived from a microorganism; a DNA encoding the protein; a recombinant DNA containing the DNA and a vector; a transformant obtained by introducing the recombinant DNA into a host cell; a method for producing a protein having a β1,3-galactosyltransferase activity using the transformant; and a method for producing a galactose-containing carbohydrate using the transformant.

10 Claims, 2 Drawing Sheets

SEQUENCE LISTING

<160> NUMBER OF SEQ ID NOS: 8

<210> SEQ ID NO 1
<211> LENGTH: 313
<212> TYPE: PRT
<213> ORGANISM: Streptococcus agalactiae Type Ib

<400> SEQUENCE: 1

Met Asn Tyr Ser Ile Ile Met Ser Val Tyr Asn Glu Pro Leu Asn Tyr
1               5                   10                  15

Val Arg Asp Ser Val Glu Ser Ile Leu Asn Gln Thr Leu Thr Asp Phe
            20                  25                  30

```
Glu Phe Ile Ile Val Ile Asp Asn Pro Ser Arg Gly Asp Leu Lys Gln
         35                  40                  45

Phe Leu Thr Glu Tyr Ser Val Val Asp Asn Arg Ile Lys Ile Leu Leu
    50                  55                  60

Asn Glu Glu Asn Ile Gly Leu Ala Ser Ser Leu Asn Lys Ala Val Lys
65                  70                  75                  80

Ile Ser Lys Gly Glu Tyr Ile Phe Arg Met Asp Ala Asp Ile Ser
                85                  90                  95

Tyr Pro Ser Arg Phe Asp Lys Gln Ile Arg Phe Met Glu Glu Asn Ser
                100                 105                 110

Leu Asp Phe Ser Ala Thr Leu Ile Glu Leu Ile Asp Gln Lys Gly Asn
        115                 120                 125

Leu Val Tyr Lys Gln Arg Glu Ser Asn Lys Ile Tyr Leu Thr Asn Asp
    130                 135                 140

Ile Arg Lys Met Leu Leu Asn Arg Ser Ile Leu Ala His Pro Thr Trp
145                 150                 155                 160

Cys Val Lys Lys Lys Val Phe Asp Lys Leu Met Gly Tyr Arg Asp Leu
                165                 170                 175

Val Pro Val Glu Asp Tyr Asp Phe Ala Ile Arg Gly Ala Leu Ala Asp
                180                 185                 190

Phe Lys Ile Gly Leu Leu Asn Lys Val Leu Leu Gln Tyr Arg Leu Asn
        195                 200                 205

Glu Asn Gly Ile Ser Gln Thr Asn Lys Phe Lys Gln Tyr Ile Tyr Ser
    210                 215                 220

Ala Ile Leu Gln Asp Phe Tyr Lys Glu Lys Ser Tyr Ile Asp Ile Thr
225                 230                 235                 240

Lys Ile Thr Asn Tyr Phe Gln Glu Tyr Val Ile Lys Lys Arg Tyr Thr
                245                 250                 255

Gln Gln Glu Leu Ser Lys Tyr Phe Glu Leu Lys Ser Thr Pro Ser Ile
                260                 265                 270

Thr Ile Arg Lys Leu Tyr Ile Cys Leu Tyr Leu Tyr Phe Lys Ser Pro
        275                 280                 285

Leu Val Arg Arg Leu Leu Ile Asn Asp Ile Asn Ile Leu Val Leu Lys
    290                 295                 300

Leu Phe Gly Gly Glu Lys Gln Ser Asp
305                 310
```

<210> SEQ ID NO 2
<211> LENGTH: 939
<212> TYPE: DNA
<213> ORGANISM: Streptococcus agalactiae Type Ib

<400> SEQUENCE: 2

```
atg aat tat agt atc att atg tcg gta tat aat gag cct tta aat tat      48
Met Asn Tyr Ser Ile Ile Met Ser Val Tyr Asn Glu Pro Leu Asn Tyr
1               5                   10                  15 gtg aga gat tca gta gaa tct ata tta aat caa acg ctt act gat ttt      96
Val Arg Asp Ser Val Glu Ser Ile Leu Asn Gln Thr Leu Thr Asp Phe
            20                  25                  30 gag ttc ata att gtc att gat aat cca agt aga ggt gat tta aag caa     144
Glu Phe Ile Ile Val Ile Asp Asn Pro Ser Arg Gly Asp Leu Lys Gln
        35                  40                  45 ttc tta aca gaa tat tca gtt gta gat aat aga ata aaa atc ttg ctt     192
Phe Leu Thr Glu Tyr Ser Val Val Asp Asn Arg Ile Lys Ile Leu Leu
    50                  55                  60 aat gaa gaa aat att ggt tta gca tca agt ttg aac aaa gcg gtg aaa     240
```

| | | | | | | | | | | | | | | | | |
|---|---|---|---|---|---|---|---|---|---|---|---|---|---|---|---|---|
| | Asn<br>65 | Glu | Glu | Asn | Ile | Gly<br>70 | Leu | Ala | Ser | Ser | Leu<br>75 | Asn | Lys | Ala | Val | Lys<br>80 |

```
att tct aag gga gaa tat att ttt aga atg gat gct gat gat att tca     288
Ile Ser Lys Gly Glu Tyr Ile Phe Arg Met Asp Ala Asp Asp Ile Ser
            85                  90                  95 tat cca agt aga ttt gat aag caa att cgt ttt atg gag gaa aat tca     336
Tyr Pro Ser Arg Phe Asp Lys Gln Ile Arg Phe Met Glu Glu Asn Ser
        100                 105                 110 ttg gat ttc tca gca act cta ata gaa ttg ata gac caa aaa gga aat     384
Leu Asp Phe Ser Ala Thr Leu Ile Glu Leu Ile Asp Gln Lys Gly Asn
    115                 120                 125 tta gta tat aaa caa cga gaa agt aat aaa ata tac tta act aat gat     432
Leu Val Tyr Lys Gln Arg Glu Ser Asn Lys Ile Tyr Leu Thr Asn Asp
130                 135                 140 ata cgg aag atg tta ttg aat aga tct ata ctt gcc cac cca acg tgg     480
Ile Arg Lys Met Leu Leu Asn Arg Ser Ile Leu Ala His Pro Thr Trp
145                 150                 155                 160 tgc gta aaa aag aaa gtt ttc gat aag tta atg gga tat aga gat tta     528
Cys Val Lys Lys Lys Val Phe Asp Lys Leu Met Gly Tyr Arg Asp Leu
                165                 170                 175 gta cct gtt gaa gat tat gat ttt gca ata aga gga gct ctg gct gat     576
Val Pro Val Glu Asp Tyr Asp Phe Ala Ile Arg Gly Ala Leu Ala Asp
            180                 185                 190 ttc aaa atc ggc tta ctc aat aaa gta ctt tta cag tat aga tta aac     624
Phe Lys Ile Gly Leu Leu Asn Lys Val Leu Leu Gln Tyr Arg Leu Asn
        195                 200                 205 gag aat gga ata tca caa acc aat aag ttt aag caa tat att tac tca     672
Glu Asn Gly Ile Ser Gln Thr Asn Lys Phe Lys Gln Tyr Ile Tyr Ser
    210                 215                 220 gct att tta caa gat ttt tat aaa gaa aaa tct tat att gat atc aca     720
Ala Ile Leu Gln Asp Phe Tyr Lys Glu Lys Ser Tyr Ile Asp Ile Thr
225                 230                 235                 240 aaa att act aat tac ttt caa gag tat gtg ata aag aaa cgc tat act     768
Lys Ile Thr Asn Tyr Phe Gln Glu Tyr Val Ile Lys Lys Arg Tyr Thr
                245                 250                 255 cag caa gag ctc tct aaa tat ttt gag cta aaa tct acc cct agt att     816
Gln Gln Glu Leu Ser Lys Tyr Phe Glu Leu Lys Ser Thr Pro Ser Ile
            260                 265                 270 act att aga aaa cta tat att tgt tta tat tta tac ttt aag tct ccc     864
Thr Ile Arg Lys Leu Tyr Ile Cys Leu Tyr Leu Tyr Phe Lys Ser Pro
        275                 280                 285 ttg gtt agg agg tta tta ata aat gat att aat att tta gta ctg aaa     912
Leu Val Arg Arg Leu Leu Ile Asn Asp Ile Asn Ile Leu Val Leu Lys
    290                 295                 300 ttg ttt gga gga gag aaa caa agt gac                                 939
Leu Phe Gly Gly Glu Lys Gln Ser Asp
305                 310

<210> SEQ ID NO 3
<211> LENGTH: 6865
<212> TYPE: DNA
<213> ORGANISM: Streptococcus agalactiae type Ib
<220> FEATURE:
<221> NAME/KEY: CDS
<222> LOCATION: (617)..(1789)
<221> NAME/KEY: CDS
<222> LOCATION: (1816)..(2262)
<221> NAME/KEY: CDS
<222> LOCATION: (2265)..(2744)
<221> NAME/KEY: CDS
<222> LOCATION: (2843)..(3979)
<221> NAME/KEY: CDS
```

```
<222> LOCATION: (3982)..(4953)
<221> NAME/KEY: CDS
<222> LOCATION: (5009)..(5947)

<400> SEQUENCE: 3
agatcttgga gatattatct gtgaaaccaa tgttcctaga ctgatggtcg ttccttcagg      60
gaaagtacca ccaaatccaa cagcattact tcagaacgct tattttaata agatgattga    120
agctattaaa aatatatttg attatattat catcgatact ccacctattg gtttagttgt    180
tgatgccgca ataatcgcta atgcttgcga tggttttatt ttagtaaccc aagcaggtag    240
aataaaacgt aattatgttg aaaaagcaaa agaacagatg gaacaaagtg gttcaaagtt    300
cttaggtatt attcttaata aagttaatga atctgttgct acttacggcg attatggaaa    360
ttacggaaaa agggatagaa aaggaagta agggctctt gtattgaaag aaaaagaaaa      420
tatacaaaag attattatag cgatgattca aaccgttgtg gtttattttt ctgcaagttt    480
gacattaaca ttaattactc ccaactttaa aagcaataaa gatttattgt tgttctatt    540 gatacattat attgtctttt atctttctga tttttacaga gacttttgga gtcgtggcta    600
tcttgaagag tttaaa atg gta ttg aaa tac agc ttt tac tat att ttc ata    652
              Met Val Leu Lys Tyr Ser Phe Tyr Tyr Ile Phe Ile
                1               5                  10 tca agt tca tta ttt ttt att tct aaa aac tct ttt aca acg aca cga    700
Ser Ser Ser Leu Phe Phe Ile Ser Lys Asn Ser Phe Thr Thr Thr Arg
         15                  20                  25 ctt tcc ttt ttt act ttt att gct atg aat tcg att tta tta tat cta    748
Leu Ser Phe Phe Thr Phe Ile Ala Met Asn Ser Ile Leu Leu Tyr Leu
     30                  35                  40 ttg aat tca ttt tta aaa tat tat cga aaa tat tct tac gct aag ttt    796
Leu Asn Ser Phe Leu Lys Tyr Tyr Arg Lys Tyr Ser Tyr Ala Lys Phe
 45                  50                  55                  60 tca cga gat acc aaa gtt gtt ttg ata acg aat aag gat tct tta tca    844
Ser Arg Asp Thr Lys Val Val Leu Ile Thr Asn Lys Asp Ser Leu Ser
                 65                  70                  75 aaa atg acc ttt agg aat aaa tac gac cat aat tat atc gct gtc tgt    892
Lys Met Thr Phe Arg Asn Lys Tyr Asp His Asn Tyr Ile Ala Val Cys
             80                  85                  90 atc ttg gat tcc tct gaa aag gat tgt tat gat ttg aaa cat aac tcg    940
Ile Leu Asp Ser Ser Glu Lys Asp Cys Tyr Asp Leu Lys His Asn Ser
         95                  100                 105 tta agg ata ata aac aaa gat gct ctt act tca gag tta acc tgc tta    988
Leu Arg Ile Ile Asn Lys Asp Ala Leu Thr Ser Glu Leu Thr Cys Leu
     110                 115                 120 act gtt gat caa gct ttt att aac ata ccc att gaa tta ttt ggt aaa   1036
Thr Val Asp Gln Ala Phe Ile Asn Ile Pro Ile Glu Leu Phe Gly Lys
125                 130                 135                 140 tac caa ata caa gat att att aat gac att gaa gca atg gga gtg att   1084
Tyr Gln Ile Gln Asp Ile Ile Asn Asp Ile Glu Ala Met Gly Val Ile
                145                 150                 155 gtc aat gtt aat gta gag gca ctt agc ttt gat aat ata gga gaa aag   1132
Val Asn Val Asn Val Glu Ala Leu Ser Phe Asp Asn Ile Gly Glu Lys
            160                 165                 170 cga atc caa act ttt gaa gga tat agt gtt att aca tat tct atg aaa   1180
Arg Ile Gln Thr Phe Glu Gly Tyr Ser Val Ile Thr Tyr Ser Met Lys
        175                 180                 185 ttc tat aaa tat agt cac ctt ata gca aaa cga ttt ttg gat atc atg   1228
Phe Tyr Lys Tyr Ser His Leu Ile Ala Lys Arg Phe Leu Asp Ile Met
    190                 195                 200
```

-continued

```
ggt gct att ata ggt ttg ctc ata tgt ggc att gtg gca att ttt cta      1276
Gly Ala Ile Ile Gly Leu Leu Ile Cys Gly Ile Val Ala Ile Phe Leu
205                 210                 215                 220 gtt ccg caa atc aga aaa gat ggt gga ccg gct atc ttt tct caa aat      1324
Val Pro Gln Ile Arg Lys Asp Gly Gly Pro Ala Ile Phe Ser Gln Asn
                225                 230                 235 aga gta ggt cgt aat ggt agg att ttt aga ttc tat aaa ttc aga tca      1372
Arg Val Gly Arg Asn Gly Arg Ile Phe Arg Phe Tyr Lys Phe Arg Ser
            240                 245                 250 atg cga gta gat gca gaa caa att aag aaa gat tta tta gtt cac aat      1420
Met Arg Val Asp Ala Glu Gln Ile Lys Lys Asp Leu Leu Val His Asn
        255                 260                 265 caa atg acg ggg cta atg ttt aag tta gac gat gat cct aga att act      1468
Gln Met Thr Gly Leu Met Phe Lys Leu Asp Asp Asp Pro Arg Ile Thr
    270                 275                 280 aaa ata gga aaa ttt att cga aaa aca agc ata gat gag ttg cct caa      1516
Lys Ile Gly Lys Phe Ile Arg Lys Thr Ser Ile Asp Glu Leu Pro Gln
285                 290                 295                 300 ttc tat aat gtt tta aaa ggt gat atg agt tta gta gga aca cgc cct      1564
Phe Tyr Asn Val Leu Lys Gly Asp Met Ser Leu Val Gly Thr Arg Pro
                305                 310                 315 ccc aca gtt gat gaa tat gaa aag tat aat tca acg cag aag cga cgc      1612
Pro Thr Val Asp Glu Tyr Glu Lys Tyr Asn Ser Thr Gln Lys Arg Arg
            320                 325                 330 ctt agt ttt aag cca gga atc act ggt ttg tgg caa ata tct ggt aga      1660
Leu Ser Phe Lys Pro Gly Ile Thr Gly Leu Trp Gln Ile Ser Gly Arg
        335                 340                 345 aat aat att act gat ttt gat gaa atc gta aag tta gat gtt caa tat      1708
Asn Asn Ile Thr Asp Phe Asp Glu Ile Val Lys Leu Asp Val Gln Tyr
    350                 355                 360 atc aat gaa tgg tct att tgg tca gat att aag att att ctc cta acg      1756
Ile Asn Glu Trp Ser Ile Trp Ser Asp Ile Lys Ile Ile Leu Leu Thr
365                 370                 375                 380 cta aag gta gtt tta ctc ggg aca gga gct aag taaaggtaag gtttgaaagg    1809
Leu Lys Val Val Leu Leu Gly Thr Gly Ala Lys
                385                 390 aatata atg aaa att tgt ctg gtt ggt tca agt ggt ggt cac cta gca       1857
       Met Lys Ile Cys Leu Val Gly Ser Ser Gly Gly His Leu Ala
                    395                 400                 405 cac ttg aac ctt ttg aaa ccc att tgg gaa aaa gaa gat agg ttt tgg      1905
His Leu Asn Leu Leu Lys Pro Ile Trp Glu Lys Glu Asp Arg Phe Trp
                410                 415                 420 gta act ttt gat aaa gaa gat gct agg agt att cta aga gaa gag att      1953
Val Thr Phe Asp Lys Glu Asp Ala Arg Ser Ile Leu Arg Glu Glu Ile
            425                 430                 435 gta tat cat tgc ttc ttt cca aca aac cgt aat gtc aaa aac ttg gta      2001
Val Tyr His Cys Phe Phe Pro Thr Asn Arg Asn Val Lys Asn Leu Val
        440                 445                 450 aaa aat act att cta gct ttt aag gtc ctt aga aaa gaa aga cca gat      2049
Lys Asn Thr Ile Leu Ala Phe Lys Val Leu Arg Lys Glu Arg Pro Asp
    455                 460                 465 gtt atc ata tca tct ggt gcc gct gta gca gta cca ttc ttt tat att      2097
Val Ile Ile Ser Ser Gly Ala Ala Val Ala Val Pro Phe Phe Tyr Ile
470                 475                 480                 485 ggt aag tta ttt ggc tgt aag acc gtt tat ata gag gtt ttc gac agg      2145
Gly Lys Leu Phe Gly Cys Lys Thr Val Tyr Ile Glu Val Phe Asp Arg
                490                 495                 500 ata gat aaa cca act ttg aca gga aaa tta gtg tat cct gta aca gat      2193
Ile Asp Lys Pro Thr Leu Thr Gly Lys Leu Val Tyr Pro Val Thr Asp
            505                 510                 515
```

```
aaa ttt att gtt cag tgg gaa gaa atg aaa aaa gtt tat cct aag gca      2241
Lys Phe Ile Val Gln Trp Glu Glu Met Lys Lys Val Tyr Pro Lys Ala
        520                 525                 530 att aat tta gga gga att ttt ta atg att ttt gtc aca gta ggg aca       2288
Ile Asn Leu Gly Gly Ile Phe     Met Ile Phe Val Thr Val Gly Thr
    535                 540                     545 cat gaa cag cag ttc aac cgt ctt att aaa gaa gtt gat aga tta aaa      2336
His Glu Gln Gln Phe Asn Arg Leu Ile Lys Glu Val Asp Arg Leu Lys
550                 555                 560 ggg aca ggt gct att gat caa gaa gtt ttc att caa acg ggt tac tca      2384
Gly Thr Gly Ala Ile Asp Gln Glu Val Phe Ile Gln Thr Gly Tyr Ser
565                 570                 575                 580 gac ttt gaa cct cag aat tgt cag tgg tca aaa ttt ctc tca tat gat      2432
Asp Phe Glu Pro Gln Asn Cys Gln Trp Ser Lys Phe Leu Ser Tyr Asp
            585                 590                 595 gat atg aac tct tac atg aaa gaa gct gag att gtt atc aca cac ggc      2480
Asp Met Asn Ser Tyr Met Lys Glu Ala Glu Ile Val Ile Thr His Gly
                600                 605                 610 ggt cca gca acg ttt atg aat gca gtt tct aaa ggg aaa aaa act att      2528
Gly Pro Ala Thr Phe Met Asn Ala Val Ser Lys Gly Lys Lys Thr Ile
            615                 620                 625 gtg gtt cct aga caa gaa cag ttt gga gag cat gtg aat aat cat cag      2576
Val Val Pro Arg Gln Glu Gln Phe Gly Glu His Val Asn Asn His Gln
    630                 635                 640 gtg gat ttt ttg aaa gag tta ttc ttg aaa tat gag tta gat tat att      2624
Val Asp Phe Leu Lys Glu Leu Phe Leu Lys Tyr Glu Leu Asp Tyr Ile
645                 650                 655                 660 ttg aat atc agt gaa tta gag aat att att aag gaa aaa aat ata tct      2672
Leu Asn Ile Ser Glu Leu Glu Asn Ile Ile Lys Glu Lys Asn Ile Ser
                665                 670                 675 act agt aaa gta ata tca caa aac aat gat ttt tgt tcc tct ttc aaa      2720
Thr Ser Lys Val Ile Ser Gln Asn Asn Asp Phe Cys Ser Ser Phe Lys
            680                 685                 690 aat gaa ctt tct aaa cta ttt gaa taaatatatt ttgttggaga aaaaaattga     2774
Asn Glu Leu Ser Lys Leu Phe Glu
        695                 700 aattaactat caatccaaag tatttgttaa taggaggaat tttcgcttta accctatttt    2834 caaagcca atg caa ctt ttg tta ctt tta gca tta ata gtt tta ctt att     2884
         Met Gln Leu Leu Leu Leu Leu Ala Leu Ile Val Leu Leu Ile
                         705                 710 tgt agt agt tat aat gaa aaa atg aaa ttt tta aat atg gct gaa att      2932
Cys Ser Ser Tyr Asn Glu Lys Met Lys Phe Leu Asn Met Ala Glu Ile
715                 720                 725                 730 ttt ttc att gta ttt tat atg gtt tat tta gta tca ata gta tta aat      2980
Phe Phe Ile Val Phe Tyr Met Val Tyr Leu Val Ser Ile Val Leu Asn
                735                 740                 745 tcg tta ttt aga agt cca gaa ttt cat aga gtc att gct gca ttc aat      3028
Ser Leu Phe Arg Ser Pro Glu Phe His Arg Val Ile Ala Ala Phe Asn
            750                 755                 760 tca ctg gca gta ggg gtt gtg tcc tta tta ttt tac cat tac tat aag      3076
Ser Leu Ala Val Gly Val Val Ser Leu Leu Phe Tyr His Tyr Tyr Lys
        765                 770                 775 aat act aat att gaa tta aca aaa ttg cta aaa tca ttt ttg ttt aat      3124
Asn Thr Asn Ile Glu Leu Thr Lys Leu Leu Lys Ser Phe Leu Phe Asn
780                 785                 790 gca att att ttg ttt tgt tta gga ttt cta tat tat tat gcc ata tat      3172
Ala Ile Ile Leu Phe Cys Leu Gly Phe Leu Tyr Tyr Tyr Ala Ile Tyr
795                 800                 805                 810
```

-continued

| | |
|---|---|
| ttt gat gta gag aat gta agt ctt ttt gga aga aat tta att gga tca<br>Phe Asp Val Glu Asn Val Ser Leu Phe Gly Arg Asn Leu Ile Gly Ser<br>815                      820                  825 | 3220 |
| gat tgg ata aat ggg atg cat acg cag aga gca atg gct ttc ttt gaa<br>Asp Trp Ile Asn Gly Met His Thr Gln Arg Ala Met Ala Phe Phe Glu<br>830                      835                  840 | 3268 |
| tat tca aat ctt ata ata ccc tta act atc ata act aat ata tat ata<br>Tyr Ser Asn Leu Ile Ile Pro Leu Thr Ile Ile Thr Asn Ile Tyr Ile<br>845                      850                  855 | 3316 |
| tat ata tat att aag caa aga tat agc tca ggg atg atg ata ctc ggt<br>Tyr Ile Tyr Ile Lys Gln Arg Tyr Ser Ser Gly Met Met Ile Leu Gly<br>860                      865                  870 | 3364 |
| gct ctt ctc tcc act att ata cta ccc atc ggg tct gga tct aga gct<br>Ala Leu Leu Ser Thr Ile Ile Leu Pro Ile Gly Ser Gly Ser Arg Ala<br>875                      880                  885                  890 | 3412 |
| ggt att ata gtt gtg cta cta cag gtt ata att tta ttg ttg aat aca<br>Gly Ile Ile Val Val Leu Leu Gln Val Ile Ile Leu Leu Leu Asn Thr<br>895                      900                  905 | 3460 |
| att gta ata aaa aga caa acg ata aga ttt ttc ctg tat tta gtt ccg<br>Ile Val Ile Lys Arg Gln Thr Ile Arg Phe Phe Leu Tyr Leu Val Pro<br>910                      915                  920 | 3508 |
| ata cta ata tta cta tta gtg ata tta cgt ttt gat aat ttg gtg agc<br>Ile Leu Ile Leu Leu Leu Val Ile Leu Arg Phe Asp Asn Leu Val Ser<br>925                      930                  935 | 3556 |
| ata tat aat aga ata atc aat ttg cgg tcg gga agt agt gaa tct aga<br>Ile Tyr Asn Arg Ile Ile Asn Leu Arg Ser Gly Ser Ser Glu Ser Arg<br>940                      945                  950 | 3604 |
| ttt tct ttg tac aag gat acc gta cac tca gta att act gac tca cta<br>Phe Ser Leu Tyr Lys Asp Thr Val His Ser Val Ile Thr Asp Ser Leu<br>955                      960                  965                  970 | 3652 |
| ttt ctg gga aaa ggt gta aaa gaa ttg tgg tta aat agt gat tta cca<br>Phe Leu Gly Lys Gly Val Lys Glu Leu Trp Leu Asn Ser Asp Leu Pro<br>975                      980                  985 | 3700 |
| cta gga tcg cat tcg acc tac ata ggt tat ttc tat aaa act ggc cta<br>Leu Gly Ser His Ser Thr Tyr Ile Gly Tyr Phe Tyr Lys Thr Gly Leu<br>990                      995                  1000 | 3748 |
| ttt gga cta ata aat gtg att tta ggt ttg ttt cta att ctt att agc<br>Phe Gly Leu Ile Asn Val Ile Leu Gly Leu Phe Leu Ile Leu Ile Ser<br>    1005                  1010                  1015 | 3796 |
| att atc aag gaa gct aaa aag tca gat ttc tat tat gag ata gta ggg<br>Ile Ile Lys Glu Ala Lys Lys Ser Asp Phe Tyr Tyr Glu Ile Val Gly<br>1020                  1025                  1030 | 3844 |
| tct gtc ata ctc cta ttt tca ttt ttt gca ctt gaa gat att gat ggc<br>Ser Val Ile Leu Leu Phe Ser Phe Phe Ala Leu Glu Asp Ile Asp Gly<br>1035                  1040                  1045                  1050 | 3892 |
| gcc aat tgg ctc att att ttt gtc ttt aca gtg ttg gga att tta gaa<br>Ala Asn Trp Leu Ile Ile Phe Val Phe Thr Val Leu Gly Ile Leu Glu<br>    1055                  1060                  1065 | 3940 |
| aat aag gat ttc tat agt caa ctt aaa agg tgg gaa agt ta atg gaa<br>Asn Lys Asp Phe Tyr Ser Gln Leu Lys Arg Trp Glu Ser    Met Glu<br>        1070                  1075                  1080 | 3987 |
| aaa caa ata ctt gtt tct atc gtt ata cct ata tac aac tcg gaa gca<br>Lys Gln Ile Leu Val Ser Ile Val Ile Pro Ile Tyr Asn Ser Glu Ala<br>    1085                  1090                  1095 | 4035 |
| tat ctt aaa gaa tgc gtg caa tcc gtc cta caa cag act cat tca ttg<br>Tyr Leu Lys Glu Cys Val Gln Ser Val Leu Gln Gln Thr His Ser Leu<br>1100                  1105                  1110 | 4083 |
| ata gaa gtt ata ctg att aat gat gga tcc act gat aat agt gga gaa<br>Ile Glu Val Ile Leu Ile Asn Asp Gly Ser Thr Asp Asn Ser Gly Glu<br>1115                  1120                  1125 | 4131 |

```
att tgt gat aat tta tct caa aaa gac gat cgc ata ctt gta ttt cat        4179
Ile Cys Asp Asn Leu Ser Gln Lys Asp Asp Arg Ile Leu Val Phe His
1130                1135                1140                1145 aaa aaa aat gga ggg gta tct tcg gca agg aac cta ggt ctt gat aaa        4227
Lys Lys Asn Gly Gly Val Ser Ser Ala Arg Asn Leu Gly Leu Asp Lys
        1150                1155                1160 tcc aca ggc gaa ttc ata acg ttt gta gat agt gat gat ttt gta gca        4275
Ser Thr Gly Glu Phe Ile Thr Phe Val Asp Ser Asp Asp Phe Val Ala
            1165                1170                1175 ccg aat ata att gaa ata atg tta aaa aat tta atc act gag gat gct        4323
Pro Asn Ile Ile Glu Ile Met Leu Lys Asn Leu Ile Thr Glu Asp Ala
        1180                1185                1190 gat ata gca gaa gta gat ttt gat att tcg aat gag aga gat tat aga        4371
Asp Ile Ala Glu Val Asp Phe Asp Ile Ser Asn Glu Arg Asp Tyr Arg
    1195                1200                1205 aag aaa aaa aga cga aac ttt tat aag gtc ttt aaa aac aat aat tct        4419
Lys Lys Lys Arg Arg Asn Phe Tyr Lys Val Phe Lys Asn Asn Asn Ser
1210                1215                1220                1225 tta aaa gaa ttt tta tca ggt aat aga gtg gaa aat att gtt tgt aca        4467
Leu Lys Glu Phe Leu Ser Gly Asn Arg Val Glu Asn Ile Val Cys Thr
        1230                1235                1240 aaa tta tat aaa aaa agt ata att ggt aac ttg agg ttt gat gag aat        4515
Lys Leu Tyr Lys Lys Ser Ile Ile Gly Asn Leu Arg Phe Asp Glu Asn
            1245                1250                1255 tta aaa att ggt gag gat tta ctt ttt aat tgt aaa att tta tgt caa        4563
Leu Lys Ile Gly Glu Asp Leu Leu Phe Asn Cys Lys Ile Leu Cys Gln
        1260                1265                1270 gag cac tgc ata gtc gta gat acg act tct tcc ttg tac acc tat cgc        4611
Glu His Cys Ile Val Val Asp Thr Thr Ser Ser Leu Tyr Thr Tyr Arg
    1275                1280                1285 atc gta aag act tct gca atg aat cag gag ttc aac gaa aat tca tta        4659
Ile Val Lys Thr Ser Ala Met Asn Gln Glu Phe Asn Glu Asn Ser Leu
1290                1295                1300                1305 gat ttt ata aca att ttt aat gaa ata agc agt att gtt cct gca aaa        4707
Asp Phe Ile Thr Ile Phe Asn Glu Ile Ser Ser Ile Val Pro Ala Lys
        1310                1315                1320 tta gct aat tat gtt gaa gcg aaa ttt tta aga gaa aag gta aag tgt        4755
Leu Ala Asn Tyr Val Glu Ala Lys Phe Leu Arg Glu Lys Val Lys Cys
            1325                1330                1335 ctc cga aaa atg ttt gaa tta ggt agt aat att gac agt aaa atc aaa        4803
Leu Arg Lys Met Phe Glu Leu Gly Ser Asn Ile Asp Ser Lys Ile Lys
        1340                1345                1350 tta caa cga gag att ttt ttc aaa gat gtt aaa tta tac cct ttc tat        4851
Leu Gln Arg Glu Ile Phe Phe Lys Asp Val Lys Leu Tyr Pro Phe Tyr
1355                1360                1365 aaa gcg gtt aag tac tta tca tta aag gga tta ttg agt att tac tta        4899
Lys Ala Val Lys Tyr Leu Ser Leu Lys Gly Leu Leu Ser Ile Tyr Leu
        1370                1375                1380                1385 atg aaa tgt tca ccc atc ttg tat ata aaa tta tat gac agg ttt caa        4947
Met Lys Cys Ser Pro Ile Leu Tyr Ile Lys Leu Tyr Asp Arg Phe Gln
            1390                1395                1400 aaa cag taagtaatca aaaattaaat taactcaatt acctttaaa ttataggagt         5003
Lys Gln tgaaa atg aat tat agt atc att atg tcg gta tat aat gag cct tta aat    5053
      Met Asn Tyr Ser Ile Ile Met Ser Val Tyr Asn Glu Pro Leu Asn
          1405                1410                1415 tat gtg aga gat tca gta gaa tct ata tta aat caa acg ctt act gat        5101
Tyr Val Arg Asp Ser Val Glu Ser Ile Leu Asn Gln Thr Leu Thr Asp
1420                1425                1430
```

-continued

| | |
|---|---|
| ttt gag ttc ata att gtc att gat aat cca agt aga ggt gat tta aag<br>Phe Glu Phe Ile Ile Val Ile Asp Asn Pro Ser Arg Gly Asp Leu Lys<br>1435                 1440                1445                1450 | 5149 |
| caa ttc tta aca gaa tat tca gtt gta gat aat aga ata aaa atc ttg<br>Gln Phe Leu Thr Glu Tyr Ser Val Val Asp Asn Arg Ile Lys Ile Leu<br>        1455                1460                1465 | 5197 |
| ctt aat gaa gaa aat att ggt tta gca tca agt ttg aac aaa gcg gtg<br>Leu Asn Glu Glu Asn Ile Gly Leu Ala Ser Ser Leu Asn Lys Ala Val<br>            1470                1475                1480 | 5245 |
| aaa att tct aag gga gaa tat att ttt aga atg gat gct gat gat att<br>Lys Ile Ser Lys Gly Glu Tyr Ile Phe Arg Met Asp Ala Asp Asp Ile<br>1485                 1490                1495 | 5293 |
| tca tat cca agt aga ttt gat aag caa att cgt ttt atg gag gaa aat<br>Ser Tyr Pro Ser Arg Phe Asp Lys Gln Ile Arg Phe Met Glu Glu Asn<br>        1500                1505                1510 | 5341 |
| tca ttg gat ttc tca gca act cta ata gaa ttg ata gac caa aaa gga<br>Ser Leu Asp Phe Ser Ala Thr Leu Ile Glu Leu Ile Asp Gln Lys Gly<br>1515                 1520                1525                1530 | 5389 |
| aat tta gta tat aaa caa cga gaa agt aat aaa ata tac tta act aat<br>Asn Leu Val Tyr Lys Gln Arg Glu Ser Asn Lys Ile Tyr Leu Thr Asn<br>            1535                1540                1545 | 5437 |
| gat ata cgg aag atg tta ttg aat aga tct ata ctt gcc cac cca acg<br>Asp Ile Arg Lys Met Leu Leu Asn Arg Ser Ile Leu Ala His Pro Thr<br>        1550                1555                1560 | 5485 |
| tgg tgc gta aaa aag aaa gtt ttc gat aag tta atg gga tat aga gat<br>Trp Cys Val Lys Lys Lys Val Phe Asp Lys Leu Met Gly Tyr Arg Asp<br>1565                 1570                1575 | 5533 |
| tta gta cct gtt gaa gat tat gat ttt gca ata aga gga gct ctg gct<br>Leu Val Pro Val Glu Asp Tyr Asp Phe Ala Ile Arg Gly Ala Leu Ala<br>1580                 1585                1590 | 5581 |
| gat ttc aaa atc ggc tta ctc aat aaa gta ctt tta cag tat aga tta<br>Asp Phe Lys Ile Gly Leu Leu Asn Lys Val Leu Leu Gln Tyr Arg Leu<br>1595                 1600                1605                1610 | 5629 |
| aac gag aat gga ata tca caa acc aat aag ttt aag caa tat att tac<br>Asn Glu Asn Gly Ile Ser Gln Thr Asn Lys Phe Lys Gln Tyr Ile Tyr<br>        1615                1620                1625 | 5677 |
| tca gct att tta caa gat ttt tat aaa gaa aaa tct tat att gat atc<br>Ser Ala Ile Leu Gln Asp Phe Tyr Lys Glu Lys Ser Tyr Ile Asp Ile<br>            1630                1635                1640 | 5725 |
| aca aaa att act aat tac ttt caa gag tat gtg ata aag aaa cgc tat<br>Thr Lys Ile Thr Asn Tyr Phe Gln Glu Tyr Val Ile Lys Lys Arg Tyr<br>1645                 1650                1655 | 5773 |
| act cag caa gag ctc tct aaa tat ttt gag cta aaa tct acc cct agt<br>Thr Gln Gln Glu Leu Ser Lys Tyr Phe Glu Leu Lys Ser Thr Pro Ser<br>1660                 1665                1670 | 5821 |
| att act att aga aaa cta tat att tgt tta tat tta tac ttt aag tct<br>Ile Thr Ile Arg Lys Leu Tyr Ile Cys Leu Tyr Leu Tyr Phe Lys Ser<br>1675                 1680                1685                1690 | 5869 |
| ccc ttg gtt agg agg tta tta ata aat gat att aat att tta gta ctg<br>Pro Leu Val Arg Arg Leu Leu Ile Asn Asp Ile Asn Ile Leu Val Leu<br>            1695                1700                1705 | 5917 |
| aaa ttg ttt gga gga gag aaa caa agt gac taatagaaaa atttatgtat<br>Lys Leu Phe Gly Gly Glu Lys Gln Ser Asp<br>1710                 1715 | 5967 |
| gtcatactct ttatcattta ttgatttgtt tatataaaga agagatatat tcaaatttag | 6027 |
| aaattattct ctcttcttct attcctgatg ttgataattt agagaaaaaa ttaaaatcaa | 6087 |
| aaacaataaa tatacatatt ttagaagaat ctagtggtga aagtgaagaa ttattatcag | 6147 |

```
tacttaaaga tgctggtcta agttatagta agtttgatag taattgtttt attttaatg      6207 atgcaacgcc tattgggagg acactaataa agcatggtat ttattataat ctaattgaag      6267
atggtttaaa ttgttttact tactctatat ttagtcaaaa actttggaag tattatgtaa      6327
aaaaatatat tcttcacaaa attcagccac atggattttc acgatattgt ttagggattg      6387
aagttaattc attagttaat ttgccaaagg atccgcgtta taaaaatttt attgaagtcc      6447
ctaggaaaga acttttgac aatgtaacag aatatcaaaa agaaatggca ataaatcttt       6507
ttggagcagt aagagttagt attaaatcac cttcagtact agtattaacg cagcctctat      6567
ctatagataa agagtttatg agttataaca ataagataga aacgtccgaa gaacaattta      6627
atttttataa atcaatagtc aatgaatata taaataaagg gtacaatgtt tatttaaaag      6687
ttcatcctag agatgtagta gattattcca aattgccggt agagctatta ccatcaaatg      6747
ttcctatgga aattatagag ttgatgttaa caggtcggtt cgaatgtggg ataacacatt      6807
cgtccactgc gctggatttt ttaacttgtg ttgataaaaa ataaacttta gtagatct        6865
```

```
<210> SEQ ID NO 4
<211> LENGTH: 27
<212> TYPE: DNA
<213> ORGANISM: Artificial Sequence
<220> FEATURE:
<223> OTHER INFORMATION: Synthetic DNA

<400> SEQUENCE: 4
gggggatcca atggtattga aatacag                                          27

<210> SEQ ID NO 5
<211> LENGTH: 29
<212> TYPE: DNA
<213> ORGANISM: Artificial Sequence
<220> FEATURE:
<223> OTHER INFORMATION: Synthetic DNA

<400> SEQUENCE: 5
aatctgcaga cttagctcct gtcccgagt                                        29

<210> SEQ ID NO 6
<211> LENGTH: 33
<212> TYPE: DNA
<213> ORGANISM: Artificial Sequence
<220> FEATURE:
<223> OTHER INFORMATION: Synthetic DNA

<400> SEQUENCE: 6
ccaagcggcc gctatagtca acttaaaagg tgg                                   33

<210> SEQ ID NO 7
<211> LENGTH: 28
<212> TYPE: DNA
<213> ORGANISM: Artificial Sequence
<220> FEATURE:
<223> OTHER INFORMATION: Synthetic DNA

<400> SEQUENCE: 7
cggctcgagt cccaataggc gttgcatc                                         28

<210> SEQ ID NO 8
<211> LENGTH: 32
<212> TYPE: DNA
<213> ORGANISM: Artificial Sequence
<220> FEATURE:
```

```
<223> OTHER INFORMATION: Synthetic DNA

<400> SEQUENCE: 8
ccggaattcg aaaaggtaaa gtgtctccga aa                              32
```

β1,3-GALACTOSYLTRANSFERASE AND DNA ENCODING THE SAME

BACKGROUND OF THE INVENTION

1. Field of the Invention

The present invention relates to a protein having a β1,3-galactosyltransferase activity, a DNA encoding the protein, a recombinant DNA containing the DNA, a transformant containing the recombinant DNA, a method for producing a protein having a β1,3-galactosyltransferase activity using the transformant, and a method for producing a galactose-containing carbohydrate using the transformant.

2. Background Art

Regarding β1,3-galactosyltransferase genes, the genes derived from higher animal (*J. Biol. Chem.*, 273: 58 (1998), *J. Biol. Chem.*, 273: 12770 (1998), *J. Biol. Chem.*, 274: 12499 (1999)) have been obtained. However, since it is generally difficult to express the genes derived from β1,3-galactosyltransferase gene derived from higher-animal has not been expressed as an active protein in a microorganism such as *Escherichia coli* or the like.

On the other hand, in microorganisms, there is a report stating that a β1,3-galactosyltransferase gene was obtained from *Campylobacter jejuni* and the gene was expressed in *Escherichia coli*. However, although this enzyme has an activity of transferring galactose to N-acetylgalactosamine, there is no report about the activity of transferring galactose to N-acetylglucosamine (*J. Biol. Chem.*, 275: 3896 (2000)).

Human milk abundantly contains galactose-containing carbohydrates, lacto-N-tetraose being one of the main components (*Acta Paediatr.*, 82: 903 (1993), *J. Pediatr. Gastroenterol. Nutr.*, 30: 181 (2000)). Since it is known that lacto-N-tetraose and lacto-N-neotetraose, which are the galactose-containing carbohydrates, are recognized by *Pseudomonas aeruginosa* (*Infect. Immun.*, 59: 700 (1991)), the galactose-containing carbohydrates are considered to be strong candidates for safe antiinfection drugs which can prevent human body from infection with *Pseudomonas aeruginosa*.

Regarding production of a galactose-containing carbohydrate such as lacto-N-tetraose or the like, both the methods of extraction from human milk and chemical synthesis are known but such methods have problems in terms of cost and productivity, so that its industrial production method has not yet been established.

SUMMARY OF THE INVENTION

An object of the present invention is to provide a protein having a β1,3-galactosyltransferase activity, and a DNA encoding the protein.

Another object of the present invention is to provide a method for producing a protein having a β1,3-galactosyltransferase activity using a transformant containing the DNA, and a method for producing a galactose-containing carbohydrate using the protein.

These and other objects have been attained by the present invention which relates to a *Streptococcus agalactiae* protein having a β1,3-galactosyltransferase activity, a DNA encoding the protein, a recombinant DNA comprising the DNA, a transformant containing the recombinant DNA, a method for producing a protein having a β1,3-galactosyltransferase activity using the transformant, and a method for producing a galactose-containing carbohydrate using the transformant.

DETAILED DESCRIPTION OF THE INVENTION

Figure 1:
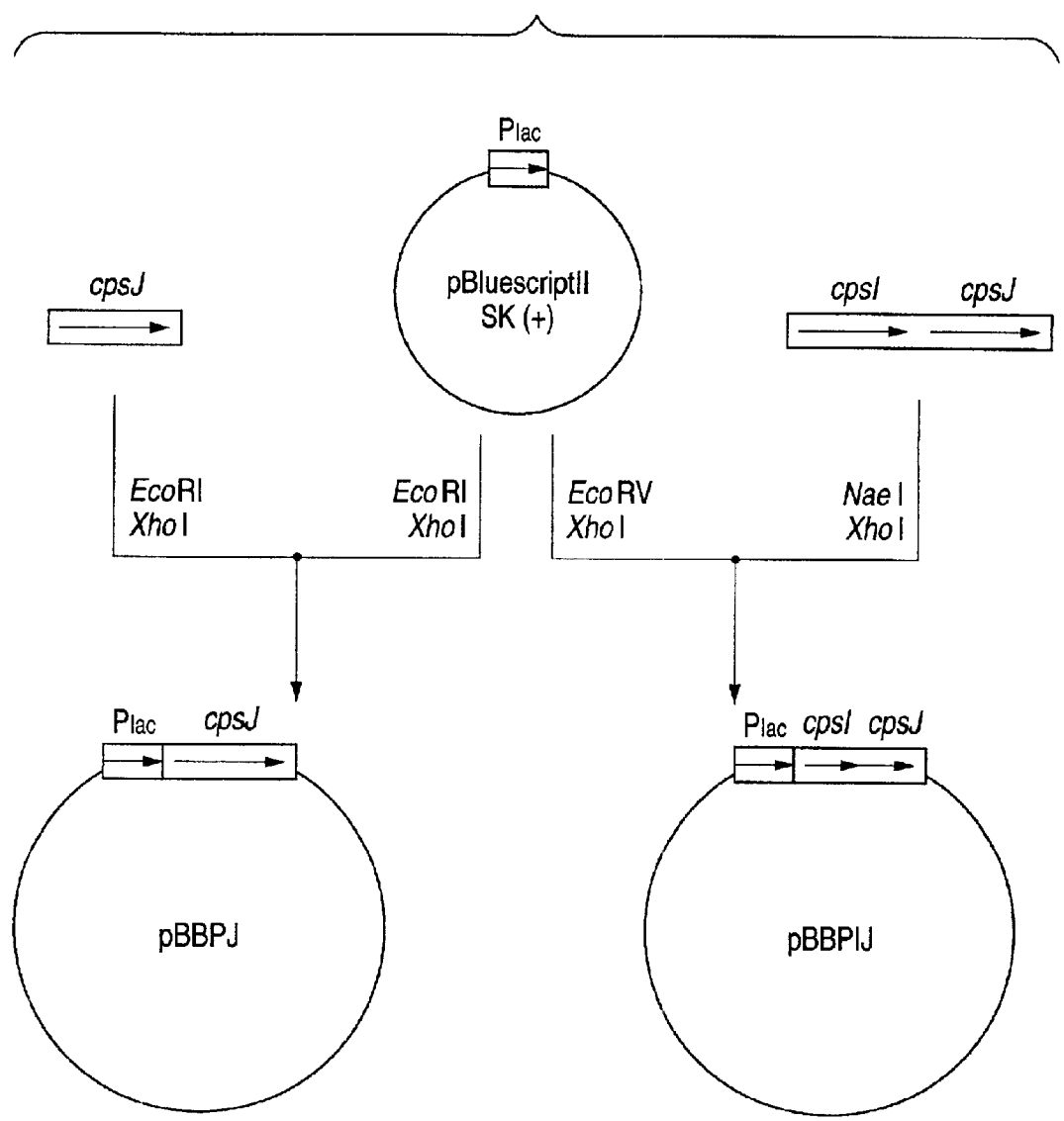
FIG. 1 shows the construction steps of β1,3-galactosyltransferase plasmids pBBPIJ and pBBPJ.

This application is based on Japanese application No. 2001-392, filed on Jan. 5, 2001, the entire content of which is incorporated herein by reference.

In order to solve the above problems, the present inventors have conducted intensive studies and found a novel β1,3-galactosyltransferase, among enzymes concerning capsular polysaccharide biosynthesis in *Streptococcus agalactiae*, and have isolated the DNA encoding such enzyme.

Specifically, the present invention relates to the following (1) to (19):

(1) A protein having a β1,3-galactosyltransferase activity derived from a microorganism having an activity of transferring galactose to N-acetylglucosamine with β1,3-linkage.

(2) The protein according to (1), wherein the microorganism belongs to the genus *Streptococcus*.

(3) The protein according to (2), wherein the microorganism is *Streptococcus agalactiae*.

(4) A protein comprising the amino acid sequence represented by SEQ ID NO: 1.

(5) A protein comprising an amino acid sequence in which at most 20 amino acids are deleted, replaced, inserted or added in the amino acid sequence represented by SEQ ID NO: 1, said protein having a β1,3-galactosyltransferase activity.

(6) A DNA encoding the protein of any one of (1) to (5).

(7) A DNA comprising the nucleotide sequence represented by SEQ ID NO: 2.

(8) A DNA which hybridizes with a DNA comprising the complementary sequence to the nucleotide sequence represented by SEQ ID NO: 2 under stringent conditions, and encodes a protein having a β1,3-galactosyltransferase activity.

(9) A recombinant DNA comprising the DNA of any one of (6) to (8) and a vector.

(10) A transformant obtained by introducing the recombinant DNA of (9) into a host cell.

(11) The transformant according to (10), wherein the host cell is a microorganism.

(12) The transformant according to (11), wherein the microorganism belongs to the genus *Escherichia*.

(13) The transformant according to (12), wherein the microorganism belonging to the genus *Escherichia* is *Escherichia coli*.

(14) A method for producing a protein having a β1,3-galactosyltransferase activity, comprising:

culturing the transformant of any one of (10) to (13) in a medium to produce and accumulate a protein having a β1,3-galactosyltransferase activity in the culture, and recovering the protein from the culture.

(15) A method for producing a galactose-containing carbohydrate, comprising:

selecting, as an enzyme source, a culture of the transformant of any one of (10) to (13) or a treated product of the culture, allowing the enzyme source, uridine-5'-diphosphogalactose and an acceptor carbohydrate to be present in an aqueous medium to produce and accumulate the galactose-containing carbohydrate in the aqueous medium, and recovering the galactose-containing carbohydrate from the aqueous medium.

(16) The method according to (15), wherein the treated product of the culture is selected from the group consisting of a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells and an enzyme preparation obtained by extracting from the cells.

(17) The method according to (15), wherein the acceptor carbohydrate is a carbohydrate having N-acetylglucosamine at its non-reducing terminal.

(18) The method according to (15), wherein the acceptor carbohydrate is selected from the group consisting of N-acetylglucosamine and lacto-N-triose II.

(19) The method according to (15), wherein the galactose-containing carbohydrate is selected from the group consisting of lacto-N-biose and lacto-N-tetraose.

The protein having a β1,3-galactosyltransferase activity of the present invention is a protein having a β1,3-galactosyltransferase activity derived from a microorganism which uses, as a substrate, an acceptor carbohydrate having N-acetylglucosamine (hereinafter referred to as "GlcNAc") on its non-reducing terminal. For example, preferred is a protein having a β1,3-galactosyltransferase activity derived from a microorganism belonging to the genus *Streptococcus*, and more preferred is a protein having a β1,3-galactosyltransferase activity derived from *Streptococcus agalactiae*.

Specifically, the protein of the present invention includes a protein comprising the amino acid sequence represented by SEQ ID NO: 1, and a protein comprising an amino acid sequence in which at most 20 amino acids are deleted, replaced, inserted or added in the amino acid sequence represented by SEQ ID NO: 1 and having a β1,3-galactosyltransferase activity.

The modified protein can readily be obtained using a method for introducing site-directed mutation(s) described in, for example, *Molecular Cloning, A Laboratory Manual*, 2nd ed., Cold Spring Harbor Laboratory Press (1989) (hereinafter referred to as "*Molecular Cloning*, 2nd ed."), *Current Protocols in Molecular Biology*, John Wiley & Sons (1987–1997) (hereinafter referred to as "*Current Protocols in Molecular Biology*"), *Nuc. Acids. Res.*, 10: 6487 (1982), *Proc. Natl. Acad. Sci. USA*, 79: 6409 (1982), *Gene*, 34: 315 (1985), *Nuc. Acids. Res.*, 13: 4431 (1985), *Proc. Natl. Acad. Sci. USA*, 82: 488 (1985) and the like. For example, the protein can be obtained by introducing mutations to DNA encoding a protein comprising the amino acid sequence represented by SEQ ID NO: 2.

The number of the amino acids which are deleted, replaced, inserted or added is not particularly limited; however, it is usually 1 to 20, preferably 1 to 10, and more preferably 1 to 5, amino acids.

The at most 20 amino acid deletion, replacement, insertion or addition in the amino acid sequence of the protein of the present invention is used herein to refer to that at most 20 amino acids are deleted, replaced, inserted or added to at one or plural positions in the amino acid sequence. The deletion, replacement, insertion or addition may be caused in the same amino acid sequence simultaneously. Also, the amino acid residue replaced, inserted or added can be natural or non-natural. Examples of the natural amino acid residue include L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine, and the like.

Herein, examples of amino acid residues which are replaced with each other are shown below. Amino acid residues in the same group can readily be replaced with each other.

Group A:
　leucine, isoleucine, norleucine, valine, norvaline, alanine, 2-aminobutanoic acid, methionine, O-methylserine, t-butylglycine, t-butylalanine, cyclohexylalanine;

Group B:
　asparatic acid, glutamic acid, isoasparatic acid, isoglutamic acid, 2-aminoadipic acid, 2-aminosuberic acid;

Group C:
　asparagine, glutamine;

Group D:
　lysine, arginine, ornithine, 2,4-diaminobutanoic acid, 2,3-diaminopropionic acid;

Group E:
　proline, 3-hydroxyproline, 4-hydroxyproline;

Group F:
　serine, threonine, homoserine;

Group G:
　phenylalanine, tyrosine.

Also, in order to have the .beta 1,3-galactosyltransferase activity of the protein of the present invention, it has preferably at least 50% or more, preferably 60% or more, still more preferably 80% or more, most preferably 95% or more, of identity to the amino acid sequence represented by SEQ ID NO: 1. The identity of a nucleotide sequence or an amino acid sequence can be determined using the algorithm "BLAST" by Karlin and Altschl (*Proc. Natl. Acad. Sci. USA*, 90: 5873–5877 (1993)). The programs called "BLASTN" and "LASTX" have developed based on the above algorithm (*J. Mol. Biol.*, 215: 403–410 (1990)). In the case of analyzing a nucleotide sequence based on BLAST, the parameter can be set to e.g. score=100, wordlength=12. And in the case of analyzing an amino acid sequence based on BLASTX, the parameter can be set to e.g. score=50, wordlength=3. In the case of using BLAST or Gapped BLAST program, a default parameter of each program can be used. The specific analysis methods of using the above programs are known in the art.

The DNA of the present invention includes a DNA encoding the protein of the present invention.

Specific examples include a DNA encoding a protein comprising the amino acid sequence represented by SEQ ID NO: 1, a DNA comprising the nucleotide sequence represented by SEQ ID NO: 2, and a DNA which hybridizes with a DNA comprising the complementary sequence to the nucleotide sequence represented by SEQ ID NO: 2 under stringent conditions and encodes a protein having a β1,3-galactosyltransferase activity.

The DNA which hybridizes under stringent conditions is a DNA obtained by colony hybridization, plaque hybridization, Southern hybridization or the like using, as a probe, the DNA comprising the complementary sequence to the nucleotide sequence represented by SEQ ID NO: 2. Specific examples include a DNA which can be identified by carrying out hybridization at 65° C. in the presence of 0.7–1.0 M NaCl using a filter on which a DNA prepared from colonies or plaques is immobilized, and then washing the filter with 0.1× to 2×SSC solution (the composition of 1×SSC contains 150 mM sodium chloride and 15 mM sodium citrate) at 65° C.

The hybridization can be carried out in accordance with a known method described in, for example, *Molecular Cloning*, 2nd ed., *Current Protocols in Molecular Biology*, *DNA Cloning 1: Core Techniques, A Practical Approach*, 2nd ed., Oxford University (1995) or the like. Specific examples of the DNA which can be hybridized include a DNA having an identity of 60% or more, preferably 80% or more, and more preferably 95% or more, with the complementary sequence to the nucleotide sequence represented by SEQ ID NO: 2 when calculated using above BLAST or the like.

The transformant which produces the protein of the present invention having a β1,3-galactosyltransferase activity can be obtained, e.g., by preparing a recombinant DNA through ligation of the DNA of the present invention to a vector DNA in accordance with the method described in *Molecular Cloning*, 2nd ed., and then transforming a host cell with the recombinant DNA in accordance with the method described in *Molecular Cloning*, 2nd ed.

The present invention is explained below in more detail.
(1) Preparation of the DNA of the present invention The DNA of the present invention is desirably prepared from a microorganism belonging to the genus *Streptococcus*. Examples of the microorganism belonging to the genus *Streptococcus* include *Streptococcus agalactiae*, such as *Streptococcus agalactiae* Type Ib and the like.

The microorganism belonging to the genus *Streptococcus* is cultured by a known method (for example, the method described in *J. Bacteriol.*, 181: 5176 (1999)).

After culturing, chromosomal DNA of the microorganism is isolated and purified by a known method (for example, method described in *Current Protocols in Molecular Biology*).

A fragment containing the DNA of the present invention can be obtained by a hybridization method, PCR or the like using a synthetic DNA designed based on a nucleotide sequence among the capsular polysaccharide biosynthesis genes of *Streptococcus agalactiae* Type III or Type Ia.

The vector to which the DNA is ligated may be any vector, such as a phage vector, a plasmid vector or the like, so long as it can replicate autonomously in *Escherichia coli* K12. Specific examples include ZAP Express (manufactured by Stratagene, Strategies, 5: 58 (1992)), pBluescript II SK(+) (manufactured by Stratagene, *Nucleic Acids Res.*, 17: 9494 (1989)), λzap II (manufactured by Stratagene), λgt10 and λgt11 (*DNA Cloning, A Practical Approach*, 1: 49 (1985)), λTriplEx (manufactured by Clontech), λExCell (manufactured by Amersham Pharmacia Biotech), pUC18 (*Gene*, 33: 103 (1985)) and the like.

Any microorganism belonging to *Escherichia coli* can be used for the host of the recombinant DNA obtained by ligating the DNA of the present invention to the above vector, so long as it is a microorganism belonging to *Escherichia coli*. Specific examples include *Escherichia coli* XL1-Blue MRF' (manufactured by Stratagene, Strategies, 5: 81 (1992)), *Escherichia coli* C600 (*Genetics*, 39: 440 (1954)), *Escherichia coli* Y1088 (*Science*, 222: 778 (1983)), *Escherichia coli* Y1090 (*Science*, 222: 778 (1983)), *Escherichia coli* NM522 (*J. Mol. Biol.*, 166: 1 (1983)), *Escherichia coli* K802 (*J. Mol. Biol.*, 16: 118 (1966)), *Escherichia coli* JM105 (*Gene*, 38: 275 (1985)) and the like.

Any method can be used in the method for introducing the recombinant DNA, so long as it is a method for introducing DNA into the selected host cell. Examples include a method using a calcium ion (*Proc. Natl. Acad. Sci. USA*, 69: 2110 (1972)), a protoplast (Japanese Published Unexamined Patent Application No. 248394/88), an electroporation (*Nucleic Acid Res.*, 16: 6127 (1988)) and the like.

The nucleotide sequence of the DNA of the present invention contained in the recombinant DNA can be determined by extracting the recombinant DNA from the thus obtained transformant. For the determination of the nucleotide sequence, a conventional method, such as the dideoxy method (*Proc. Natl. Acad. Sci. USA*, 74: 5463 (1977)) or an apparatus for nucleotide sequence analysis, such as DNA Sequencer 373A (manufactured by Perkin-Elmer) or the like, can be used.

The DNA of interest can also be prepared by chemical synthesis based on the thus determined nucleotide sequence using, for example, DNA Synthesizer 8905 Type manufactured by Perceptive Biosystems or the like.

Examples of transformant containing the thus obtained recombinant DNA include *Escherichia coli* JM109/pBBPJ containing a plasmid DNA having the nucleotide sequence represented by SEQ ID NO: 2.
(2) Preparation of the Protein of the Present Invention.

The protein of the present invention can be produced by expressing the DNA of the present invention obtained by the method of (1) in a host cell, for example, as shown below, using a method described in *Molecular Cloning*, 2nd ed., *Current Protocols in Molecular Biology* or the like.

When the DNA of the present invention is used, a DNA fragment of a suitable length containing a portion which encodes the protein of the present invention can be prepared, if necessary. In addition, productivity of the protein can be improved by substituting a nucleotide of the protein-coding portion of the nucleotide sequence so that it has the most suitable codons for the expression in the host.

The transformant which expresses the DNA of the present invention can be obtained by inserting the DNA into a downstream of the promoter of a suitable expression vector to thereby prepare a recombinant DNA, and introducing the recombinant DNA into a host cell suitable for the expression vector.

Any bacteria, yeasts, animal cells, insect cells, plant cells, and the like can be used as the host cell so long as it can express the gene of interest.

Examples of the expression vector include those which can replicate autonomously in the above-described host cell or can be integrated into chromosome and have a promoter at such a position that the DNA of the present invention can be transcribed.

When a procaryote cell, such as a bacterium or the like, is used as the host cell, it is preferred that the recombinant DNA containing the DNA of the present invention can replicate autonomously in the bacterium. It is also preferred that the recombinant vector contains a promoter, a ribosome binding sequence, the DNA of the present invention and a transcription termination sequence. A gene regulating the promoter may also be desirably contained therewith in operable combination.

Examples of the expression vector include pHelixl (manufactured by Roche Diagnostics), pKK223-3 (manufactured by Amersham Pharmacia Biotech), pSE280 (manufactured by Invitrogen), pGEMEX-1 (manufactured by Promega), pQE-8 (manufactured by QIAGEN), pET-3 (manufactured by Novagen), pKYP10(Japanese Published Unexamined Patent Application No. 110600/83), pKYP200 (Agric. Biol. Chem., 48: 669 (1984)), pLSA1 (Agric. Biol. Chem., 53: 277 (1989)), pGEL1 (Proc. Natl. Acad. Sci. USA, 82: 4306 (1985)), pbluescript II SK(+) (manufactured by Stratagene), pTrs30(prepared from Escherichia coli JM109/pTrS30 (FERM BP-5407)), pTrs32 (prepared from Escherichia coli JM109/pTrS32 (FERM BP-5408)), pPAC31 (WO 98/12343), pUC19 (Gene, 33: 103 (1985)), pSTV28 (manufactured by Takara Shuzo), pUC118 (manufactured by Takara Shuzo), pPA1 (Japanese Published Unexamined Patent Application No. 233798/88), and the like.

Any promoter can be used so long as it can function in the host cell. Examples include promoters derived from Escherichia coli, phage and the like, such as trp promoter (Ptrp), Iac promoter (Plac), $P_L$ promoter, $P_R$ promoter, $P_{SE}$ promoter, etc., SPO1 promoter, SPO2 promoter, penP promoter and the like. Also, artificially designed and modified promoters, such as a promoter in which two Ptrp are linked in tandem (Ptrp×2), tac promoter, lacT7 promoter letI promoter and the like, can be used.

It is preferred to use a plasmid in which the space between Shine-Dalgarno sequence, which is the ribosome binding sequence, and the initiation codon is adjusted to an appropriate distance (for example, 6 to 18 base pairs).

The transcription termination sequence is not always necessary for the expression of the DNA of the present invention. However, it is preferred to provide a transcription terminating sequence just downstream of the structural gene.

Examples of the procaryote cell include microorganisms belonging to the genera Escherichia, Serratia, Bacillus, Brevibacterium, Corynebacterium, Microbacterium, Pseudomonas, Streptococcus and the like. Specific examples include Escherichia coli XL1-Blue, Escherichia coli XL2-Blue, Escherichia coli DH1, Escherichia coli MC1000, Escherichia coli KY3276, Escherichia coli W1485, Escherichia coli JM109, Escherichia coli HB101, Escherichia coli No. 49, Escherichia coli W3110, Escherichia coli NY49, Serratia ficaria, Serratia fonticola, Serratia liquefaciens, Serratia marcescens, Bacillus subtilis, Bacillus megaterium, Bacillus amyloliquefaciens, Brevibacterium immariophilum ATCC 14068, Brevibacterium saccharolyticum ATCC 14066, Corynebacterium ammoniagenes, Corynebacterium glutamicum ATCC 13032, Corynebacterium glutamicum ATCC 14067, Corynebacterium glutamicum ATCC 13869, Corynebacterium acetoacidophilum ATCC 13870, Microbacterium ammoniaphilum ATCC 15354, Pseudomonas sp. D-0110, Streptococcus agalactiae Type Ia, Streptococcus agalactiae Type Ib, Streptococcus agalactiae Type III, Streptococcus pneumoniae Type 14, and the like.

With regard to the method for the introduction of the recombinant DNA, any method for introducing DNA into the above-described host cells, such as a method using a calcium ion (Proc. Natl. Acad. Sci. USA, 69: 2110 (1972)), a protoplast (Japanese Published Unexamined Patent Application No. 248394/88), an electroporation (Nucleic Acids Res., 16: 6127 (1988)) and the like, can be used.

When yeast is used as the host cell, examples of the expression vector include YEp13 (ATCC 37115), YEp24 (ATCC 37051), YCp50(ATCC 37419), pHS19, pHS15, and the like.

Any promoter can be used so long as it can function in yeast. Examples include PHO5 promoter, PGK promoter, GAP promoter, ADH promoter, gal 1 promoter, gal 10 promoter, a heat shock polypeptide promoter, MFα1 promoter, CUP 1 promoter and the like.

Examples of the host cell include yeast strains belonging to the genera Saccharomyces, Schizosaccharomyces, Kluyveromyces, Trichosporon, Schwanniomyces, Pichia, Candida and the like. Specific examples include Saccharomyces cerevisiae, Schizosaccharomyces pombe, Kluyveromyces lactis, Trichosporon pullulans, Schwanniomyces alluvius, Pichia pastoris, Candida utilis and the like.

With regard to the method for the introduction of the recombinant DNA, any method for introducing DNA into yeast, such as an electroporation (Methods. Enzymol., 194: 182 (1990)), a spheroplast method (Proc. Natl. Acad. Sci. USA, 75: 1929 (1978)), a lithium acetate method (J. Bacteriol., 153: 163 (1983)) and the like, can be used.

When an animal cell is used as the host cell, examples of the expression vector include pcDNAI and pcDM8 (manufactured by Funakoshi), pAGE107 (Japanese Published Unexamined Patent Application No. 22979/91), pAS3-3 (Japanese Published Unexamined Patent Application No. 227075/90), pcDM8 (Nature, 329: 840 (1987)), pcDNAI/Amp (manufactured by Invitrogen), pREP4 (manufactured by Invitrogen), pAGE103 (J. Biochem., 101: 1307 (1987)), pAGE210, pAMo, pAMoA and the like.

Any promoter can be used so long as it can function in an animal cell. Examples include a promoter of IE (immediate early) gene of cytomegalovirus (CMV), an early promoter of SV40, a metallothionein promoter, a promoter of retrovirus, a heat shock promoter, SRα promoter, and the like. Also, the enhancer of the IE gene of human CMV can be used together with the promoter.

Examples of the host cell include mouse myeloma cell, rat myeloma cell, mouse hybridoma cell, human Namalwa cell, Namalwa KJM-1 cell, human fetal kidney cell, human leukemia cell, African grivet kidney cell, Chinese hamster ovary (CHO) cell HST5637 (Japanese Published Unexamined Patent Application No. 299/88) and the like.

Examples of the mouse myeloma cell include SP2/0, NS0 and the like. Examples of the rat myeloma cell include YB2/0 and the like. Examples of the human fetal kidney cell include HEK293 (ATCC: CRL-1573) and the like. Examples of the human leukemia cell include BALL-1 and the like. Examples of the African grivet kidney cell include COS-1, COS-7 and the like.

The method for introduction of the recombinant DNA into animal cells is not particularly limited, so long as it is the general method for introducing DNA into animal cells, such as an electroporation (Cytotechnology, 3: 133 (1990)), a calcium phosphate method (Japanese Published Unexamined Patent Application No. 227075/90), a lipofection (Proc. Natl. Acad. Sci. USA, 84, 7413 (1987)), the method described in Virology, 52: 456 (1973) and the like.

When an insect cell is used as the host cell, the protein can be expressed by a known method described in, for example, Baculovirus Expression Vectors, A Laboratory Manual, W. H. Freeman and Company, New York (1992), Molecular Biology, A Laboratory Manual, Current Protocols in Molecular Biology, Bio/Technology, 6: 47 (1988) or the like.

Specifically, a transfer vector containing the DNA to make it express and baculovirus are co-transfected into an insect cell to obtain a recombinant virus in a supernatant of the culture of its insect cell, and then an insect cell is infected with the resulting recombinant virus to express the protein.

Examples of the transfer vector used in the method include pVL1392, pVL1393 and pBlueBacIII (all manufactured by Invitrogen), and the like.

Examples of the baculovirus include Autographa californica nuclear polyhedrosis virus which infects insects of the family Barathra and the like.

Examples of the insect cell include *Spodoptera frugiperda* ovary cell, *Trichoplusia ni* ovary cell, *Bombyx mori* ovary-derived culturing cell and the like.

Examples of *Spodoptera frugiperda* ovary cells include Sf9 and Sf21 (*Baculovirus Expression Vectors, A Laboratory Manual*) and the like. Examples of *Trichoplusia ni* ovary cells include High 5 and BTI-TN-5B1-4 (manufactured by Invitrogen) and the like. Examples of the cell line derived from silkworm ovary cellinclude *Bombyx mori* N4 and the like.

The methods for co-transfecting the above transfer vector and the above baculovirus for the preparation of the recombinant virus include a calcium phosphate method (Japanese Published Unexamined Patent Application No. 227075/90), a lipofection (*Proc. Natl. Acad. Sci. USA*, 84: 7413 (1987)), and the like.

When a plant cell is used as the host cell, examples of expression vector include Ti plasmid, a tobacco mosaic virus vector, and the like.

Any promoter can be used so long as it can function in a plant cell. Examples include 35S promoter of cauliflower mosaic virus (CaMV), rice actin 1 promoter, and the like.

Examples of the host cells include plant cells and the like, such as tobacco, potato, tomato, carrot, soybean, rape, alfalfa, rice, wheat, barley, and the like.

The method for introducing the recombinant DNA is not particularly limited, so long as it is the general method for introducing DNA into a plant cell, such as the *Agrobacterium* method (Japanese Published Unexamined Patent Application No. 140885/84, Japanese Published Unexamined Patent Application No. 70080/85, WO 94/00977), the electroporation (Japanese Published Unexamined Patent Application No. 251887/85), the particle gun method (Japanese Patents 2606856 and 2517813), and the like.

The gene can be expressed as a secretory protein or a fusion protein and the like in accordance with the methods described in *Molecular Cloning*, 2nd ed., in addition to direct expression.

When expressed in yeast, an animal cell or an insect cell, a glycosylated protein can be obtained.

The protein of the present invention can be produced by culturing the thus obtained transformant of the present invention in a medium to produce and accumulate the protein in the culture, and recovering the protein from the culture.

Culturing of the transformant of the present invention in a medium is carried out according to the conventional method as used in culturing of the host.

As a medium for culturing the transformant obtained by using, as the host, prokaryote (such as *Escherichia coli* or the like) or eukaryote (such as yeast or the like), the medium may be either a natural medium or a synthetic medium, so long as it contains a carbon source, a nitrogen source, an inorganic salt and the like which can be assimilated by the organism and the transformant can be cultured efficiently.

Examples of the carbon source which can be assimilated by the transformant include carbohydrates (for example, glucose, fructose, sucrose, molasses containing them, starch, starch hydrolysate, etc.), organic acids (for example, acetic acid, propionic acid, etc.), alcohols (for example, ethanol, propanol, etc.), and the like.

Examples of the nitrogen source include ammonia, various ammonium salts of inorganic acids or organic acids (for example, ammonium chloride, ammonium sulfate, ammonium acetate, ammonium phosphate, etc.), other nitrogen-containing compounds, peptone, meat extract, yeast extract, corn steep liquor, casein hydrolysate, soybean meal and soybean meal hydrolysate, various fermented cells and hydrolysates thereof, and the like.

Examples of the inorganic salt include potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

Culturing is usually carried out under aerobic conditions by shaking culture, submerged spinner culture under aeration or the like. The culturing temperature is preferably from 15 to 40° C., and the culturing time is generally from 5 hours to 7 days. The pH of the medium is preferably maintained at 3.0 to 9.0 during culturing. The pH can be adjusted using an inorganic or organic acid, an alkali solution, urea, calcium carbonate, ammonia, or the like.

Also, antibiotics such as ampicillin, tetracycline, and the like, can be added to the medium during culturing, if necessary.

When a microorganism transformed with an expression vector containing an inducible promoter is cultured, an inducer can be added to the medium, if necessary. For example, isopropyl-β-D-thiogalactopyranoside (IPTG) or the like can be added to the medium when a microorganism transformed with an expression vector containing lac promoter is cultured, or indoleacrylic acid or the like can by added thereto when a microorganism transformed with an expression vector containing trp promoter is cultured.

Examples of the medium for culturing a transformant obtained using an animal cell as the host include generally used RPMI 1640 medium (*The Journal of the American Medical Association*, 199: 519 (1967)), Eagle's MEM (*Science*, 122: 501 (1952)), DMEME (*Virology*, 8: 396 (1959)), and 199 Medium (*Proceeding of the Society for the Biological Medicine*, 73: 1 (1950)), as well as other media to which fetal calf serum or the like has been added to the above media and the like.

Culturing is generally carried out under conditions at pH 6 to 8 and at 30 to 40° C. for 1 to 7 days in the presence of 5% $CO_2$ or the like.

Furthermore, if desired, antibiotics such as kanamycin, penicillin, streptomycin and the like, can be added to the medium during culturing.

Examples of the medium for culturing a transformant obtained using an insect cell as the host include generally used TNM-FH medium (manufactured by Pharmingen), Sf-900 II SFM (manufactured by Life Technologies), ExCell 400 and ExCell 405 (both manufactured by JRH Biosciences), Grace's Insect Medium (*Nature*, 195: 788 (1962)) and the like.

Culturing is generally carried out under conditions at pH 6 to 7 and at 25 to 30° C. for 1 to 5 days or the like.

Furthermore, if desired, antibiotics such as gentamicin and the like, can be added to the medium during culturing.

A transformant obtained using a plant cell as the host cell can be used as the cell or after differentiating to a plant cell or organ. Examples of the medium used in culturing of the transformant include Murashige and Skoog (MS) medium, White medium, media to which a plant hormone, such as auxin, cytokinine, or the like has been added, and the like.

Culturing is carried out generally at a pH 5 to 9 and at 20 to 40°C. for 3 to 60 days.

Also, antibiotics such as kanamycin, hygromycin and the like, can be added to the medium during culturing, if necessary.

As described above, the protein can be produced by culturing a transformant derived from a microorganism, animal cell or plant cell containing a recombinant DNA to which a DNA encoding the protein of the present invention has been inserted according to the general culturing method to produce and accumulate the protein, and recovering the protein from the culture.

The method for producing the protein of the present invention includes a method of intracellular expression in a host cell, a method of extracellular secretion from a host cell, or a method of production on an outer membrane of the host cell. The method can be selected by changing the host cell employed or the structure of the protein produced.

When the protein of the present invention is produced in a host cell or on an outer membrane of the host cell, the protein can be actively secreted extracellularly according to, for example, the method of Paulson et al. (*J. Biol. Chem.*, 264: 17619 (1989)), the method of Lowe et al. (*Proc. Natl. Acad. Sci. USA*, 86: 8227 (1989); *Genes Develop.*, 4: 1288 (1990)), or the methods described in Japanese Published Unexamined Patent Application Nos. 336963/93, 823021/94, and the like.

Specifically, the protein of the present invention can be actively secreted extracellularly by expressing it in the form that a signal peptide has been added to the side of N-terminal of a protein containing an active site of the protein of the present invention according to the recombinant DNA technique.

Furthermore, the amount produced can be increased using a gene amplification system, such as by use of a dihydrofolate reductase gene or the like according to the method described in Japanese Published Unexamined Patent Application No. 227075/90.

Moreover, the protein of the present invention can be produced by a transgenic animal (transgenic nonhuman animal) or plant (transgenic plant).

When the transformant is the nonhuman animal individual or plant individual, the protein of the present invention can be produced by breeding or cultivating it so as to produce and accumulate the protein, and recovering the protein from the nonhuman animal individual or plant individual.

Examples of the method for producing the protein of the present invention using the nonhuman animal individual include a method for producing the protein of the present invention in a nonhuman animal developed by introducing a gene according to known methods (*Am. J. Clin. Nutr.*, 63: 639S (1996), *Am. J. Clin. Nutr.*, 63: 627S (1996), *Bio/Technology*, 9: 830 (1991)).

In the nonhuman animal individual, the protein can be produced by breeding a transgenic nonhuman animal to which the DNA encoding the protein of the present invention has been introduced to produce and accumulate the protein in the animal, and recovering the protein from the animal. Examples of the production and accumulation place in the animal include milk (Japanese Published Unexamined Patent Application No. 309192/88), egg and the like of the animal. Any promoter can be used, so long as it can function in the animal. Suitable examples include an α-casein promoter, a β-casein promoter, β-lactoglobulin promoter, a whey acidic protein promoter, and the like, which are specific for mammary glandular cells.

Examples of the method for producing the protein of the present invention using the plant individual include a method for producing the protein of the present invention by cultivating a transgenic plant to which the DNA encoding the protein of the present invention is introduced by a known method (*Tissue Culture*, 20 (1994), *Tissue Culture*, 21 (1994), *Trends in Biotechnol.*, 15: 45 (1997)) to produce and accumulate the protein in the plant, and recovering the protein from the plant.

The protein produced by the transformant of the present invention can be isolated and purified using the general method for isolating and purifying an enzyme.

For example, when the protein of the present invention is expressed as a soluble product in the host cells, the cells are collected by centrifugation after culturing, suspended in an aqueous buffer, and disrupted using an ultrasonicator, a French press, a Manton Gaulin homogenizer, a Dynomill, or the like to obtain a cell-free extract.

From the supernatant obtained by centrifuging the cell-free extract, a purified product can be obtained by the general method used for isolating and purifying an enzyme, for example, solvent extraction, salting-out using ammonium sulfate or the like, desalting, precipitation using an organic solvent, anion exchange chromatography using a resin, such as diethylaminoethyl (DEAE)-Sepharose, DIAION HPA-75 (manufactured by Mitsubishi Chemical) or the like, cation exchange chromatography using a resin, such as S-Sepharose FF (manufactured by Pharmacia) or the like, hydrophobic chromatography using a resin, such as butyl sepharose, phenyl sepharose or the like, gel filtration using a molecular sieve, affinity chromatography, chromatofocusing, or electrophoresis, such as isoelectronic focusing or the like, alone or in combination thereof.

When the protein is expressed as an inclusion body in the host cells, the cells are collected in the same manner, disrupted and centrifuged to recover the protein as the precipitate fraction. Next, the inclusion body of the protein is solubilized with a protein-denaturing agent.

The solubilized protein solution is diluted or dialyzed to lower the concentration of the protein denaturing agent in the solution. Thus, the normal tertiary structure of the protein is reconstituted. After the procedure, a purified product of the protein can be obtained by a purification/isolation method similar to the above.

When the protein of the present invention or its glycosylated-derivative is secreted out of cells, the protein or its derivative can be collected in the culture supernatant.

Namely, the culture supernatant is obtained by treating the culture medium in a treatment similar to the above, such as centrifugation or the like. Then a purified product can be obtained from the supernatant using a purification/isolation method similar to the above.

Examples of the protein obtained by the above method include a protein comprising the amino acid sequence represented by SEQ ID NO: 1.

Furthermore, a fusion protein of the protein of the present invention and other protein is produced, and can be purified using affinity chromatography using a substance having affinity to the fusion protein. For example, the protein of the present invention is produced as a fusion protein with protein A according to the method of Lowe et al. (*Proc. Natl. Acad. Sci. USA*, 86: 8227 (1989); *Genes Develop.*, 4: 1288 (1990)), or the method described in Japanese Published Unexamined Patent Application No. 336963/93 or WO 94/23021, and it can be purified by affinity chromatography using immunoglubulin G.

Moreover, the protein of the present invention is produced as a fusion protein with Flag peptide, and the fusion protein can be purified by affinity chromatography using an anti-Flag antibody (*Proc. Natl. Acad. Sci., USA*, 86: 8227 (1989)). Further purification can be carried out by affinity chromatography using the antibody against the protein per se.

Also, based on the information of the thus obtained protein, the protein of the present invention can be produced by a chemical synthesis method, such as Fmoc (fluorenylmethyloxycarbonyl) method, tBoc (t-butyloxycarbonyl) method, or the like. It can also be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

(3) Preparation of Galactose-Containing Carbohydrate

A galactose-containing carbohydrate can be produced in an aqueous medium using a culture of the transformant obtained by culturing described in (2) or a treated product of the culture as the enzyme source.

Examples of the treated product of culture include a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells, an enzyme preparation obtained by extracting from the cell, and the like.

The enzyme source for use in the production of a galactose-containing carbohydrate is used in a concentration of 1 mU/l to 1,000 U/l, preferably 10 mU/l to 100 U/l, when the activity capable of forming 1 μmol of galactose-containing carbohydrate at 37° C. in 1 minute is defined as 1 unit (U).

Examples of the aqueous medium for use in the production of a galactose-containing carbohydrate include water, buffer solutions (for example, phosphate buffer, carbonate buffer, acetate buffer, borate buffer, citrate buffer, tris bufrer, etc.), alcohols (for example, methanol, ethanol, etc.), esters (for example, ethyl acetate, etc.), ketones (for example, acetone, etc.), amides (for example, acetamide, etc.), and the like. Also, the culture of the microorganisms used as the enzyme source can be used as an aqueous medium.

In producing a galactose-containing carbohydrate, a surfactant or an organic solvent may be added, if necessary. Any surfactant capable of accelerating the formation of a galactose-containing carbohydrate may be used as the surfactant. Examples include nonionic surfactants (for example, polyoxyethylene octadecylamine (e.g., Nymeen S-215, manufactured by Nippon Oil & Fats), etc.), cationic surfactants (for example, cetyltrimethylammonium bromide, alkyldimethyl benzylammoniumchloride (e.g., Cation F2-40E, manufactured by Nippon Oil & Fats), etc.), anionic surfactants (for example, lauroyl sarcosinate, etc.), tertiary amines (for example, alkyldimethylamine (e.g., Tertiary Amine FB, manufactured by Nippon Oil & Fats), etc.), and the like, which are used alone or as a mixture of two or more. The surfactant is used generally in a concentration of 0.1 to 50 g/l. Examples of the organic solvent include xylene, toluene, fatty acid alcohol, acetone, ethyl acetate, and the like, which are used in a concentration of generally 0.1 to 50 ml/l.

The galactose-containing carbohydrate formation reaction is carried out in an aqueous medium having a pH 5 to 10, preferably 6 to 8, at 20 to 50° C. for 1 to 96 hours. In this formation reaction, inorganic salts, such as $MnCl_2$, $MgCl_2$ and the like, can be added, if necessary.

The amount of the galactose-containing carbohydrate produced in the aqueous medium can be determined, for example, using a High-performance anion-exchange chromatography with pulsed amperometric detection system manufactured by Dionex (Anal. Biochem., 189: 151 (1990)).

The galactose-containing carbohydrate produced in the aqueous medium can be collected by the ordinary methods using activated carbon, ion exchange resins, and the like.

The present invention is explained based on the examples, but the scope of the present invention is not limited thereto.

BEST MODE FOR CARRYING OUT THE INVENTION

EXAMPLE 1

Isolation of DNA Containing β1,3-Galactosyltransferase Gene (1) Cloning of Capsular Polysaccharide Biosynthesis Genes from *Streptococcus agalactiae* Type Ia (1)

*Streptococcus agalactiae* Type Ia was cultured by the method described in *J. Bacteriol.*, 181: 5176 (1999). After collecting the cells by centrifugation, chromosomal DNA of the microorganism was isolated and purified in accordance with the method described in *Current Protocols in Molecular Biology*.

DNAs having the nucleotide sequences represented by SEQ ID NOs:4 and 5 which had been designed based on the nucleotide sequence around the cpsD gene which is one of the capsular polysaccharide biosynthesis genes of *Streptococcus agalactiae* Type III (*Mol. Microbiol.*, 8: 843 (1993)) were synthesized using a DNA synthesizer Model 8905 manufactured by Perceptive Biosystems. Using these synthetic DNAs as a primer set, PCR was carried out using the chromosomal DNA of *Streptococcus agalactiae* Type Ia as the template. The PCR was carried out using 40 μl of a reaction solution containing 0.1 μg of the chromosomal DNA, 0.5 μmol/l each primer, 2.5 units of TaKaRa LA Taq polymerase (manufactured by Takara Shuzo), 4 μl of a buffer solution for TaKaRa LA Taq polymerase and 200 μmol/l each deoxyNTP and repeating a reaction step consisting of 1 minute at 94° C., 2 minutes at 42° C. and 3 minutes at 72° C. 30 times. A probe was prepared by labeling the thus amplified fragment using Random Primer DNA Labeling Kit (manufactured by Takara Shuzo).

Fragments obtained by digesting the chromosomal DNA of *Streptococcus agalactiae* Type Ia with a restriction enzyme EcoRI were ligated to pBluescript II SK(+) to prepare recombinant DNAs, and a library was prepared by transforming *E. coli* JM109 with these recombinant DNAs.

Using the above probe and library, colony hybridization was carried out according to the method known by persons having ordinary skill in the art to obtain a strain of clone showing a strong signal. A plasmid contained in this strain was named pBA101 and its structure was analyzed to find that it was a structure in which a 3.5 kb fragment derived from the chromosomal DNA of *Streptococcus agalactiae* Type Ia was inserted into pBluescript II SK(+). The nucleotide sequence of the DNA was determined according to the method known by persons having ordinary skill in the art, and as a result, the three genes named cpsIaf, cpsIag and cpsIaH, and a part of a gene named cpsIaE described in *J. Bacteriol.*, 181: 5176 (1999) were found in the DNA, so that it was confirmed that the DNA contains a part of the capsular polysaccharide biosynthesis genes. Also, as a result of homology search, it was confirmed that the cpsIaE gene and the cpsIaG gene had high homology with the glucosyltransferase gene and with the β1,4-galactosyltransferase gene, respectively (FIG. 1).

(2) Cloning of Capsular Polysaccharide Biosynthesis Gene from *Streptococcus agalactiae* Type Ia (2)

The 3.5 kb fragment of *Streptococcus agalactiae* Type Ia, which had been inserted into the plasmid pBA101 obtained in (1) of Example 1, was labeled using Random Primer DNA Labeling Kit (manufactured by Takara Shuzo) to prepare a probe.

Fragments obtained by digesting the chromosomal DNA of *Streptococcus agalactiae* Type Ia with a restriction enzyme BglII were ligated to pBluescript II SK(+) to prepare recombinant DNAs, and a library was prepared by transforming *E. coli* JM109 with these recombinant DNAs.

Using the above probe and library, colony hybridization was carried out so as to obtain a strain of clone showing a strong signal. A plasmid contained in this strain was named pBA103 and its structure was analyzed to find that it was a structure in which a 3.1 kb DNA derived from the chromosomal DNA of *Streptococcus agalactiae* Type Ia was inserted into pBluescript II SK(+). When the nucleotide sequence of the 3.1 kb DNA was determined according to the method known by persons having ordinary skill in the art, genes named cpsIaI and cpsIaJ and a part of the cpsIaH gene were found in the DNA, and it was confirmed that the DNA contained in pBA103 was a DNA adjacent to the DNA contained in pBA101 on the chromosomal DNA and that pBA103 is also a plasmid which contains a part of the DNA of the capsular polysaccharide biosynthesis genes. As a result of homology search, it was confirmed that the cpsIaI gene and the cpsIaj gene have high homology with the β1,3-N-acetylglucosaminyltransferase gene and the β1,4-galactosyltransferase gene, respectively (FIG. 1, *J. Bacteriol.*, 181: 5176 (1999)).

(3) Isolation of DNA Containing β1,3-galactosyltransferase gene from *Streptococcus agalactiae* Type Ib The 3.1 kb fragment of *Streptococcus agalactiae* Type Ia, which had been inserted into the plasmid pBA103 obtained in (2) of Example 1, was labeled using Random Primer DNA Labeling Kit (manufactured by Takara Shuzo) to prepare a probe.

*Streptococcus agalactiae* Type Ib was cultured by the method described in *J. Bacteriol.*, 181: 5176 (1999). After collecting the cells by centrifugation, chromosomal DNA of the microorganism was isolated and purified in accordance with the method described in *Current Protocols in Molecular Biology*.

Fragments obtained by digesting the chromosomal DNA of *Streptococcus agalactiae* Type Ib with a restriction enzyme BglII were introduced into pBluescript II SK(+) and transformed into *E. coli* JM109 to prepare a library.

Using the above probe and library, colony hybridization was carried out to obtain two cloned strains showing a strong signal. Plasmids contained in these strains were named pBB102 and pBB103, respectively, and their structures were analyzed to find that they were structures in which 5.5 and 1.4 kb fragments derived from the chromosomal DNA of *Streptococcus agalactiae* Type Ib were inserted into pBluescript II SK(+), respectively (FIG. 1).

When the nucleotide sequences of these two DNAs were determined according to the method known by persons having ordinary skill in the art, it was determined that these two DNAs were present by adjacent to each other on the chromosomal DNA and having the continued nucleotide sequence represented by SEQ ID NO: 3. It was revealed that genes named cpsIbE, cpsIbF, cpsIbG, cpsIbH, cpsIbI and cpsIbJ are present in the DNA having the nucleotide sequence represented by SEQ ID NO: 3. As a result of homology search, the cpsIbE gene showed high homology with the cpsIaE gene and the glucosyltransferase gene, the cpsIbG gene with the cpsIaG gene and the β1,4-galactosyltransferase gene, and the cpsIbI gene with the cpsIaI gene and the β1,3-N-acetylgalactosaminyltransferase gene. Accordingly, it was confirmed that the DNA having the nucleotide sequence represented by SEQ ID NO: 3 contains a part of the capsular polysaccharide biosynthesis genes in *Streptococcus agalactiae* Type Ib.

Also, it was considered that the cpsIbJ gene is a gene comprising a DNA encoding a protein having a β131,3-galactosyltransferase activity because the protein encoded by the cpsIbJ gene having the nucleotide sequence represented by SEQ ID NO: 2 has a preserved sequence of a glycosyltransferase but its homology with the cpsIaJ gene is low, a cpsIaj gene product takes a role in transferring galactose in the capsular polysaccharide biosynthesis in *Streptococcus agalactiae* Type Ia (*J. Bacteriol.*, 181: 5176 (1999)), and the linkages of galactose of capsular polysaccharide in *Streptococcus agalactiae* Type Ia and *Streptococcus agalactiae* Type Ib are different, which are β1,4 and β1,3, respectively (*J. Bacteriol.*, 181: 5176 (1999)). The amino acid sequence of the protein encoded by this DNA is shown in SEQ ID NO: 1.

EXAMPLE 2

Construction of a Strain Expressing β1,3-galactosyltransferase gene:

A DNA containing the galactosyltransferase gene obtained in (3) of Example 1 was amplified by the following method using DNAs having the nucleotide sequences represented by SEQ ID NOs: 6 and 7 synthesized using DNA Synthesizer Model 8905 manufactured by Perceptive Biosystems.

PCR was carried out using these synthesized DNAs as a primer set and the *Streptococcus agalactiae* Type Ib chromosomal DNA as the template. Using 40 μl of a reaction solution containing 0.1 μg of the chromosomal DNA, 0.5 μmol/l each primer, 2.5 units of TaKaRa LA Taq polymerase (manufactured by Takara Shuzo), 4 μl of a buffer solution for TaKaRa LA Taq polymerase and 200 μmol/l each deoxyNTP, PCR was carried out by repeating a step of 94° C. for 1 minute, 42° C. for 2 minutes and 72° C. for 3 minutes 30 times.

After confirming amplification of the fragment of interest by subjecting 1/10 volume of the reaction solution to agarose gel electrophoresis, the amplified fragment was recovered from the remaining reaction solution using GeneClean II Kit (manufactured by Bio 101) and then dissolved in TE buffer (10 mmol/l Tris-HCl and 1 mmol/l EDTA (pH 8.0)) to obtain 20 μl of the DNA solution.

Using 5 μl of the dissolved solution, the DNA was digested with restriction enzymes NotI and XhoI, the resulting DNAs were separated using agarose gel electrophoresis and then a DNA of 2.0 kb was recovered using GeneClean II Kit.

After 0.2 μg of pBluescript II SK(+) DNA was digested with restriction enzymes NotI and XhoI, the resulting DNAs were separated by agarose gel electrophoresis and then a DNA of 3.0 kb was recovered using GeneClean II Kit.

Using a ligation kit, the 2.0 kb and 3.0 kb fragments were ligated at 16° C. for 16 hours.

Using the ligation reaction solution, *E. coli* JM109 was transformed in accordance with the method known by persons having ordinary skill in the art, and the transformants were spread on LB agar medium (10 g/l Bacto Tryptone (manufactured by Difco), 10 g/l Yeast Extract (manufactured by Difco), 5 g/l sodium chloride, 15 g/l agar) containing 50 μg/ml ampicillin, followed by culturing overnight at 37° C.

Figure 2:
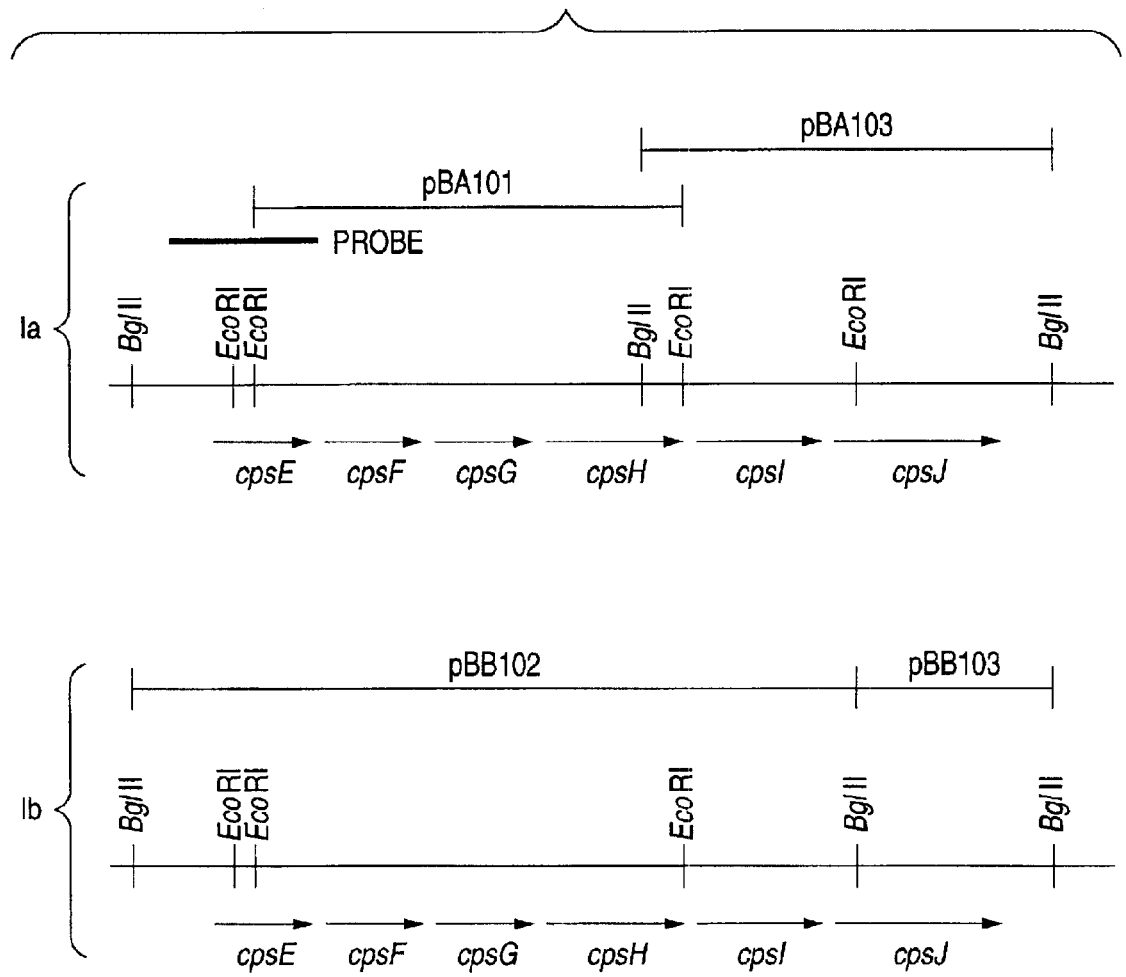
FIG. 2 shows the structure of capsular polysaccharide biosynthesis genes in *Streptococcus agalactiae* Type Ia and Type Ib.

By extracting plasmid from the thus grown transformant colonies in accordance with the method known by persons having ordinary skill in the art, an expression plasmid PBBPIJ was obtained. The structure of this plasmid was confirmed by restriction enzyme digestion (FIG. 2).

In the same manner, PCR was carried out using DNAs having the nucleotide sequences represented by SEQ ID NOs: 7 and 8 synthesized using DNA Synthesizer Model 8905 manufactured by Perceptive Biosystems as a primer set and the *Streptococcus agalactiae* type Ib chromosomal DNA as the template.

After confirming amplification of the fragment of interest by subjecting 1/10 volume of the reaction solution to agarose gel electrophoresis, the amplified fragment was recovered from the remaining reaction solution using GeneClean II Kit (manufactured by Bio 101) to obtain 20 µl TE solution of the DNA.

Using 5 µl of the solution, the DNA was digested with restriction enzymes EcoRI and XhoI, the resulting DNAs were separated by agarose gel electrophoresis and then a DNA of 1.0 kb was recovered using GeneClean II Kit.

After 0.2 µg of pBluescript II SK(+) DNA was digested with restriction enzymes EcoRI and XhoI, the resulting DNAs were separated by agarose gel electrophoresis and then a DNA of 3.0 kb was recovered using GeneClean II Kit.

Using a ligation kit, the 1.0 kb and 3.0 kb fragments were ligated at 16° C. for 16 hours.

Using the ligation reaction solution, *E. coli* JM109 was transformed in accordance with the method known by persons having ordinary skill in the art, and the transformants were spread on LB agar medium containing 50 µg/ml ampicillin, followed by culturing overnight at 37° C.

By extracting plasmid from the thus grown transformant colonies in accordance with the method known by persons having ordinary skill in the art, an expression plasmid pBBPJ was obtained. The structure of this plasmid was confirmed by restriction enzyme digestion (FIG. 2).

*Escherichia coli* JM109/pBBPJ having the plasmid pBBPJ containing a DNA encoding a protein having a β1,3-galactosyltransferase activity derived from *Streptococcus agalactiae* Type Ib has been deposited as FERM BP-7400 on Dec. 21, 2000 in National Institute of Bioscience and Human-Technology, Agency of Industrial Science and Technology (1–3, Higashi 1-chome, Tsukuba-shi, Ibaraki-ken, 305-8566 Japan) (present name and address: International Patent Organism Depositary, National Institute of Advanced Industrial Science and Technology (AIST Tsukuba Central 6, 1—1, Higashi 1-chome Tsukuba-shi, Ibaraki-ken, 305-8566 Japan)).

EXAMPLE 3
Production of Lacto-N-Tetraose

Each of the *Escherichia coli* JM109/pBBPIJ and JM109/pBBPJ obtained in Example 2 was inoculated into a test tube charged with 8 ml of LB medium containing 50 µg/ml ampicillin respectively, followed by culturing at 37° C. for 17 hours. The culture was inoculated at 1% into a test tube charged with 8 ml of LB medium containing 50 µg/ml ampicillin respectively, followed by culturing at 37° C. for 5 hours, and then IPTG was added thereto to give a concentration of 1 mmol/l. Two hours after additional culturing, wet cells were obtained by centrifugation. A membrane fraction was prepared from the wet cells in accordance with the method known by persons having ordinary skill in the art (*J. Biol. Chem.*, 272: 19502 (1997), *Mol. Microbiol.*, 26: 197 (1997)). Since this membrane fraction can be stored at −80° C., if necessary, it was able to use it by thawing prior to use.

Lacto-N-triose II to be used as the acceptor carbohydrate was prepared by allowing lacto-N-neotetraose (manufactured by Sigma) to react with β-galactosidase (manufactured by Seikagaku Corporation), completely removing the non-reducing terminal galactose and then inactivating the β-galactosidase activity by heat treatment at 100° C. for 5 minutes.

The reaction was carried out at 37° C. for 72 hours in 0.1 ml of a reaction solution containing the JM109/pBBPIJ membrane fraction (200 µg/ml), 50 mmol/l citrate buffer (pH 7.0), 5 mmol/l $MgCl_2$, 10 mmol/l lacto-N-triose II and 5 mmol/l UDP-galactose.

After completion of the reaction, the reaction product was analyzed using a High-performance anion-exchange chromatography with pulsed amperometric detection system manufactured by Dionex (DX-500) under the following analyzing conditions to confirm that 0.2 mmol/l lacto-N-tetraose was produced and accumulated in the reaction solution.

In the same manner, it was confirmed that 0.05 mmol/l lacto-N-tetraose was produced and accumulated when a JM109/pBBJ membrane fraction was used.

Analyzing conditions

| | |
|---|---|
| Column: | CarboPAC PA10 |
| Eluent: | A; $H_2O$, B; 500 mmol/l NaOH |
| Gradient: | 10 to 70% B in 20 min |
| Detector: | Pulsed amperometric detector |

While the invention has been described in detail and with reference to specific embodiments thereof, it will be apparent to one skilled in the art that various changes and modifications can be made therein without departing from the spirit and scope thereof. All references cited herein are incorporated, by reference, in their entirety.

What is claimed is:

1. An isolated or purified protein comprising the amino acid sequence represented by SEQ ID NO: 1.

2. An isolated or purified protein comprising an amino acid sequence in which at most 20 amino acids are deleted, replaced or added in the amino acid sequence represented by SEQ ID NO: 1, said protein having a β1,3-galactosyltransferase activity.

3. A method for producing a protein according to claim 1 or 2, comprising:
   culturing a transformant harboring a recombinant DNA encoding said protein in a medium to produce and accumulate said protein in culture, and
   recovering the protein from the culture.

4. The method according to claim 3, wherein said recombinant DNA comprises a vector.

5. The method according to claim 4, wherein said transformant is a microorganism.

6. The method according to claim 5, wherein said microorganism belongs to the genus *Escherichia*.

7. The method according to claim 6, wherein said microorganism is *Escherichia coli*.

8. A method for producing a galactose-containing carbohydrate, comprising:
   allowing the protein according to claim 1 or 2, uridine-5'-diphosphogalactose and an acceptor carbohydrate which has N-acetylglucosamine at its non-reducing end terminal to be present in an aqueous medium to produce and accumulate the galactose-containing carbohydrate in the aqueous medium, and
   recovering the galactose-containing carbohydrate from the aqueous medium.

9. The method according to claim 8, wherein the acceptor carbohydrate is N-acetylglucosamine or lacto-N-triose II.

10. The method according to claim 8, wherein the galactose-containing carbohydrate is lacto-N-biose or lacto-N-tetraose.

* * * * *